(12) United States Patent
Alonso Babarro

(10) Patent No.: US 12,376,740 B2
(45) Date of Patent: Aug. 5, 2025

(54) AIRWAY MANIPULATOR DEVICES

(71) Applicant: Airway Medical Innovations Pty Ltd, Queensland (AU)

(72) Inventor: Julio Miguel Alonso Babarro, Queensland (AU)

(73) Assignee: Airway Medical Innovations Pty Ltd, Queensland (AU)

(*) Notice: Subject to any disclaimer, the term of this patent is extended or adjusted under 35 U.S.C. 154(b) by 605 days.

(21) Appl. No.: 17/621,612

(22) PCT Filed: Jun. 25, 2019

(86) PCT No.: PCT/AU2019/050659
§ 371 (c)(1),
(2) Date: Dec. 21, 2021

(87) PCT Pub. No.: WO2020/000034
PCT Pub. Date: Jan. 2, 2020

(65) Prior Publication Data
US 2022/0395170 A1 Dec. 15, 2022

(51) Int. Cl.
*A61B 1/267* (2006.01)
*A61B 1/00* (2006.01)
*A61M 16/04* (2006.01)

(52) U.S. Cl.
CPC .......... *A61B 1/267* (2013.01); *A61B 1/00066* (2013.01); *A61M 16/0488* (2013.01)

(58) Field of Classification Search
CPC ....... A61B 17/24; A61B 17/28; A61B 17/282; A61B 1/00066; A61M 16/0488
See application file for complete search history.

(56) References Cited

U.S. PATENT DOCUMENTS 2,756,742 A 7/1956 Barton
3,316,913 A * 5/1967 Swenson ........... A61M 16/0488
604/93.01
(Continued)

FOREIGN PATENT DOCUMENTS

DE 202012003341 U1 8/2012
EP 1542578 B1 6/2005
(Continued)

OTHER PUBLICATIONS

International Preliminary Report on Patentability in International Appln. No. PCT/AU2019/050659, dated Dec. 28, 2021, 9 pages.
(Continued)

*Primary Examiner* — Tuan V Nguyen
(74) *Attorney, Agent, or Firm* — Fish & Richardson P.C.

(57) ABSTRACT

A device for insertion into an airway of a subject, the device including: an arm defining a distal end and a proximal end, the arm including: an elongate handle portion at the proximal end, the handle portion extending substantially towards the distal end, and an offset portion located between the distal end and the handle portion, the offset portion being offset dorsally relative to the handle portion and the distal end; and a tip at the distal end of the arm, wherein the arm is configured to allow a user to hold the handle portion outside of a mouth of the subject and move the handle portion to move the tip through the mouth and pharynx of the subject to thereby position the tip proximate to a larynx of the subject.

24 Claims, 29 Drawing Sheets

(56) References Cited

U.S. PATENT DOCUMENTS

| | | | |
|---|---|---|---|
| 4,069,820 | A | 1/1978 | Berman |
| 5,184,603 | A | 2/1993 | Stone |
| 5,197,463 | A | 3/1993 | Jeshuran |
| 5,509,408 | A | 4/1996 | Kurtis |
| 5,643,221 | A | 7/1997 | Bullard |
| 5,694,929 | A | 12/1997 | Christopher |
| 5,776,052 | A | 7/1998 | Callahan |
| 5,964,217 | A | 10/1999 | Christopher |
| 6,251,069 | B1 | 6/2001 | Mentzelopoulos et al. |
| 6,568,388 | B2 | 5/2003 | Christopher |
| 6,763,831 | B2 | 7/2004 | Sniadach |
| 7,438,717 | B2 | 10/2008 | Tylke |
| 7,608,040 | B1 | 10/2009 | Dunst |
| 8,960,195 | B2 | 2/2015 | Lehman |
| 9,364,631 | B2 | 6/2016 | Tylke |
| 10,531,792 | B2 | 1/2020 | Babarro et al. |
| 2003/0047189 | A1 | 3/2003 | Kumar |
| 2006/0276694 | A1 | 12/2006 | Acha Gandarias |
| 2009/0044799 | A1 | 2/2009 | Qui |
| 2009/0211574 | A1 | 8/2009 | Sniadach |
| 2010/0191062 | A1 | 7/2010 | Kieffer |
| 2010/0249513 | A1 | 9/2010 | Tydlaska |
| 2010/0261967 | A1 | 10/2010 | Pacey et al. |
| 2013/0333232 | A1 | 12/2013 | Kildevaeld |
| 2014/0000622 | A1 | 1/2014 | Azagury |
| 2014/0135787 | A1 | 5/2014 | Tylke |
| 2014/0144432 | A1 | 5/2014 | Avitsian |
| 2014/0173912 | A1 | 6/2014 | Scimone |
| 2014/0332000 | A1 | 11/2014 | Stegman et al. |
| 2014/0336676 | A1 | 11/2014 | Pong |
| 2015/0283344 | A1 | 10/2015 | Olympio |
| 2015/0314094 | A1 | 11/2015 | Avitsian et al. |
| 2015/0336782 | A1 | 11/2015 | Boyajian |
| 2016/0114117 | A1 | 4/2016 | Cook |
| 2017/0325667 | A1 | 11/2017 | Babarro et al. |
| 2018/0104427 | A1 | 4/2018 | Avitsian et al. |
| 2018/0169365 | A1 | 6/2018 | Sawyer et al. |
| 2018/0207383 | A1 | 7/2018 | Gardner |
| 2018/0272090 | A1 | 9/2018 | Blom |
| 2019/0059710 | A1 | 2/2019 | Molnar |
| 2020/0352429 | A1 | 11/2020 | Babarro et al. |
| 2022/0257889 | A1 | 8/2022 | Babarro |
| 2022/0355052 | A1 | 11/2022 | Babarro |
| 2022/0355053 | A1 | 11/2022 | Babarro |
| 2023/0270963 | A1 | 8/2023 | Babarro et al. |

FOREIGN PATENT DOCUMENTS

| | | |
|---|---|---|
| EP | 2679144 A1 | 1/2014 |
| EP | 3150245 A2 | 4/2017 |
| GB | 2332375 A | 6/1999 |
| JP | 2012-196300 A | 10/2012 |
| JP | 2013-502961 A | 1/2013 |
| JP | 2013-192820 A | 9/2013 |
| KR | 20140130355 A | 11/2014 |
| KR | 101508839 B1 | 4/2015 |
| WO | WO 2001/091838 A1 | 12/2001 |
| WO | WO 2003/047673 A1 | 6/2003 |
| WO | WO 2009/026095 A1 | 2/2009 |
| WO | WO 2011/023930 A1 | 3/2011 |
| WO | WO 2011/119521 A1 | 9/2011 |
| WO | WO 2014084769 | 6/2014 |
| WO | WO 2016090435 | 6/2016 |
| WO | WO 2018109033 | 6/2018 |
| WO | WO 2020/000031 A1 | 1/2020 |

OTHER PUBLICATIONS

International Search Report and Written Opinion in International Appln. No. PCT/AU2019/050659, dated Jan. 2, 2020, 14 pages.
AU Australian Examination Report No. 1 for AU Appln. No. 2019204961, mailed on Sep. 10, 2020, 4 pages.
AU First Examination Report in AU Application No. 2015362090, mailed on Feb. 1, 2017, 2 pages.
AU First Examination Report in AU Application No. 2017251785, mailed on Apr. 6, 2018, 3 pages.
AU Office Action in Australian Appln. No. 2019295405, mailed on Feb. 17, 2025, 5 pages.
AU Office Action in Australian Appln. No. 2019295406, mailed on Dec. 23, 2024, 3 pages.
AU Office Action in Australian Appln. No. 2020302956, mailed on Feb. 27, 2025, 3 pages.
CN Office Action in Chinese Appln. No. 201580074269.7, mailed on Feb. 18, 2020, 12 pages (with English Translation).
CN Office Action in Chinese Appln. No. 201580074269.7, mailed on Jun. 19, 2019, 11 pages (with English Translation).
CN Office Action with English Translation, CN Appln. No. 201580074269.7, Aug. 28, 2018, 17 pages.
EP Extended Search Report in European Appln. No. 19825304.9, mailed on Jan. 23, 2023, 8 pages.
EP Supplemental European Search Report in European Appln. No. 15867493.7, mailed on Jun. 29, 2018, 8 pages.
Glide Rite AutoStylet Brochure, Verathon Inc., Jan. 2010, 2 pages.
JP Office Action in Japanese Appln. No. 2021-576822, mailed on Jun. 18, 2024, 9 pages (with English translation).
PCT International Preliminary Report on Patentability in International Appln. No. PCT/AU2015/050786, mailed on Dec. 21, 2016, 7 pages.
PCT International Preliminary Report on Patentability in International Appln. No. PCT/AU2019/050652, mailed on Dec. 28, 2021, 8 pages.
PCT International Preliminary Report on Patentability in International Appln. No. PCT/AU2019/050653, mailed on Dec. 28, 2021, 5 pages.
PCT International Preliminary Report on Patentability in International Appln. No. PCT/AU2020/050639, mailed on Dec. 28, 2021, 10 pages.
PCT International Preliminary Report on Patentability in International Appln. No. PCT/AU2020/050640, mailed on Aug. 24, 2020, 9 pages.
PCT International Search Report and Written Opinion in International Appln. No. PCT/AU2015/050786, Feb. 17, 2016.
PCT International Search Report and Written Opinion in International Appln. No. PCT/AU2019/050652, mailed on Jul. 26, 2019, 17 pages.
PCT International Search Report and Written Opinion in International Appln. No. PCT/AU2019/050653, mailed on Sep. 16, 2019, 8 pages.
PCT International Search Report and Written Opinion in International Appln. No. PCT/AU2020/050639, mailed on Aug. 10, 2020, 14 pages.
PCT International Search Report and Written Opinion in International Appln. No. PCT/AU2020/050640, mailed on Dec. 13, 2022, 4 pages.
US Office Action in U.S. Appl. No. 17/621,544, mailed on Jan. 29, 2025, 33 pages.
US Office Action in U.S. Appl. No. 17/621,608, mailed on Aug. 21, 2024, 32 pages.
US Restriction Requirement in U.S. Appl. No. 17/621,612, mailed on Apr. 23, 2024, 7 pages.

\* cited by examiner

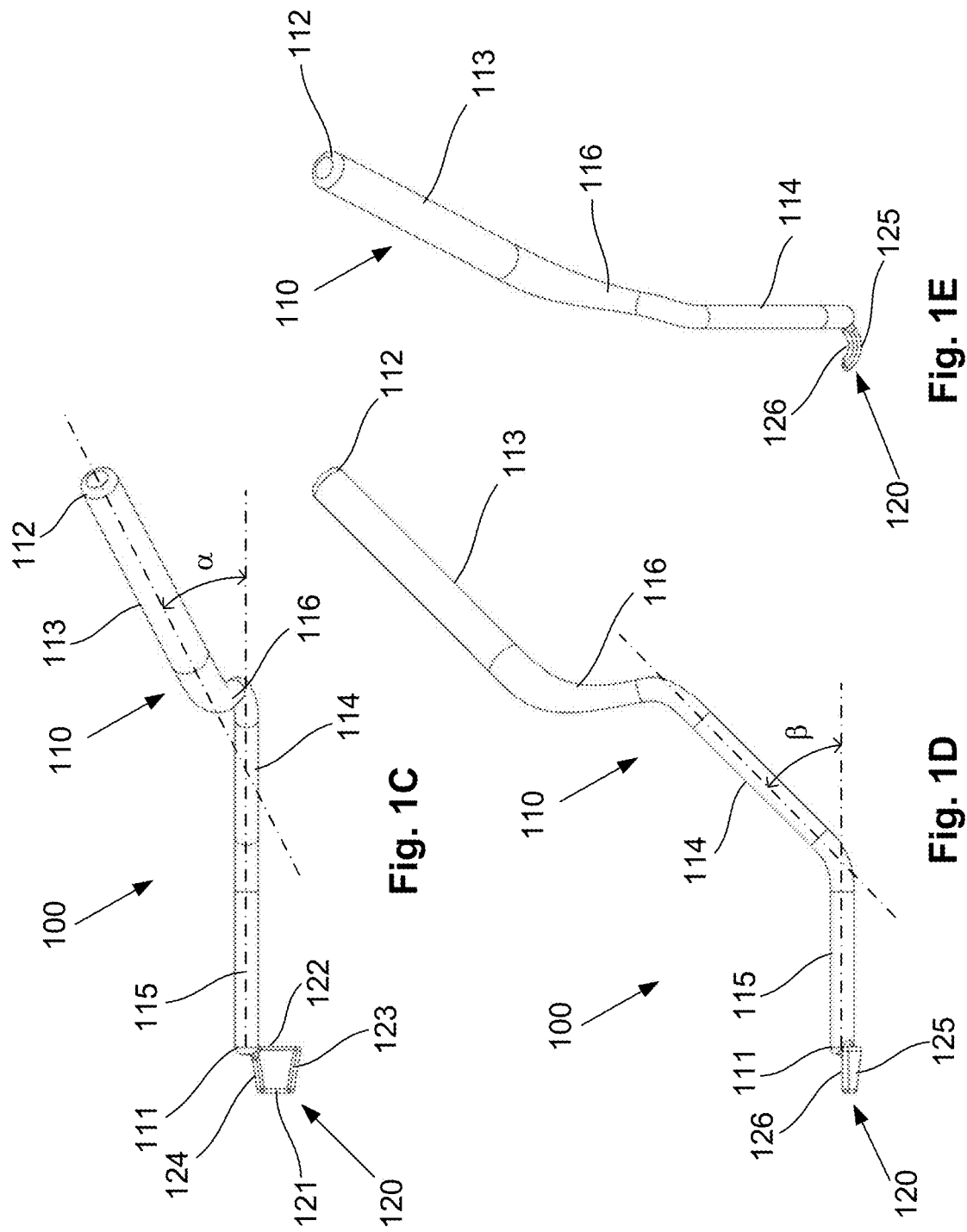

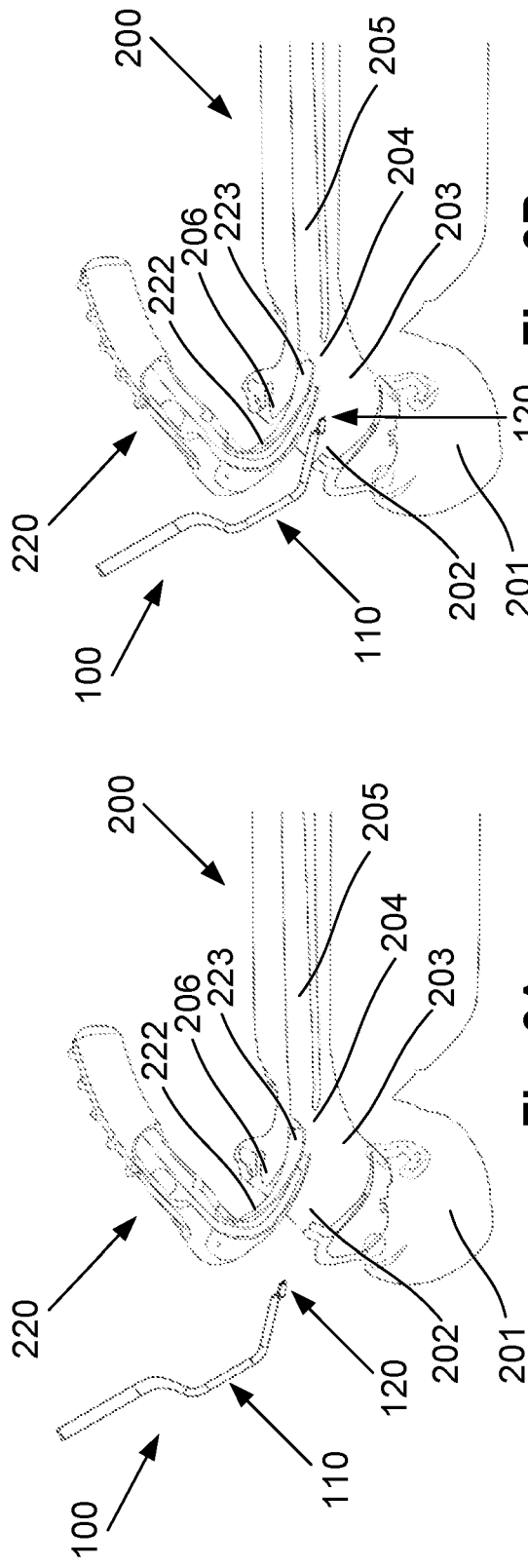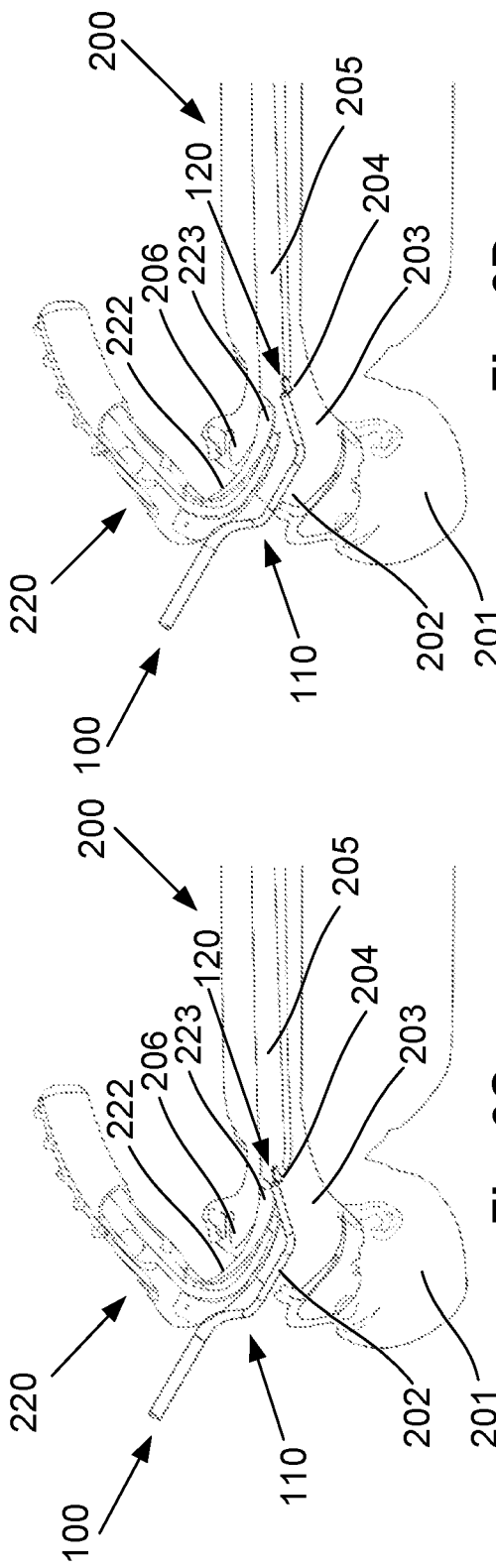

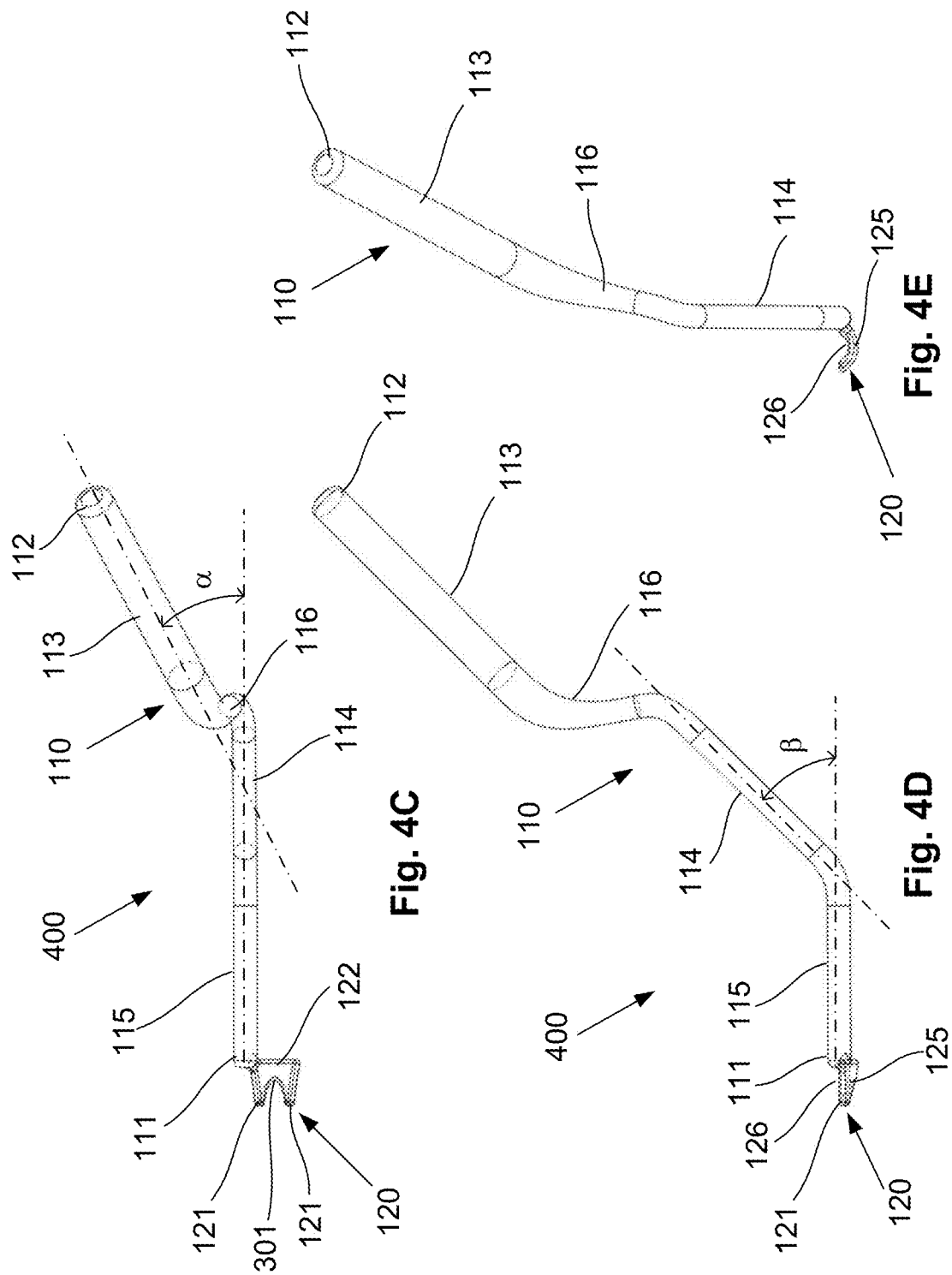

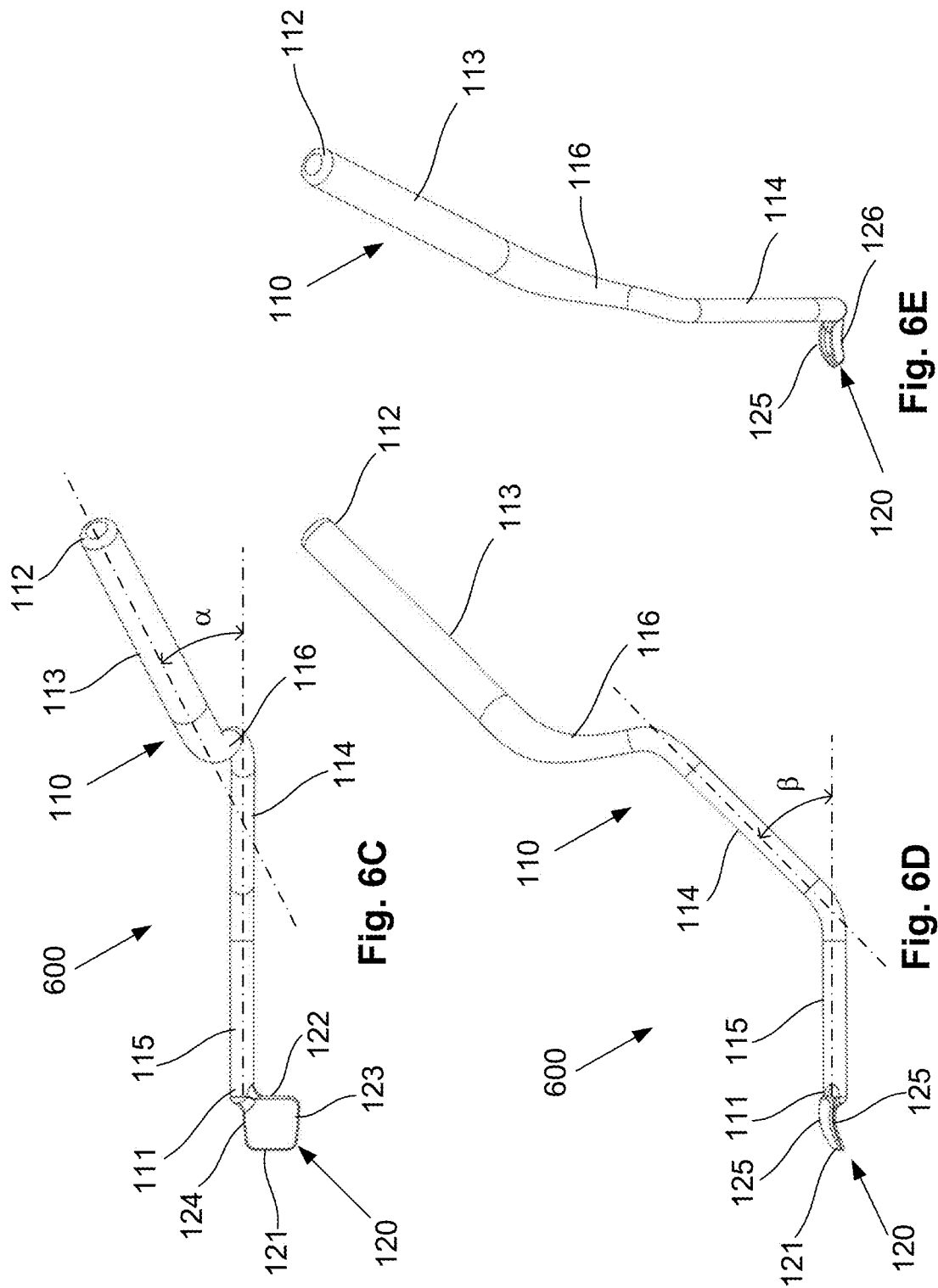

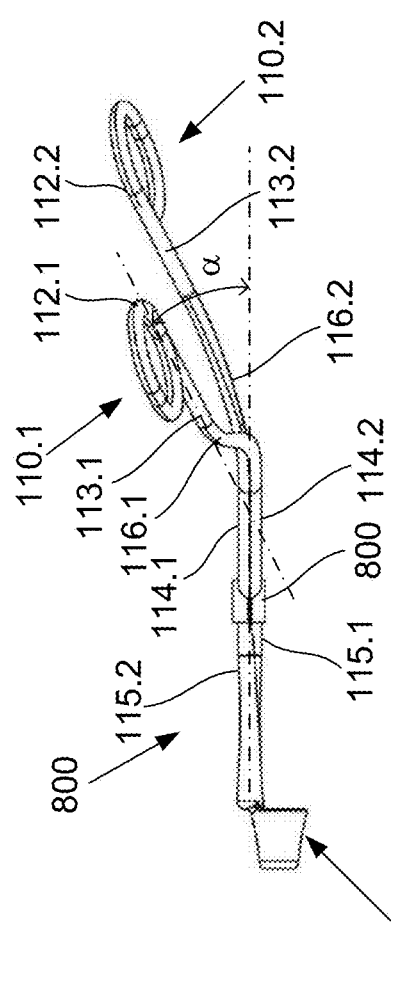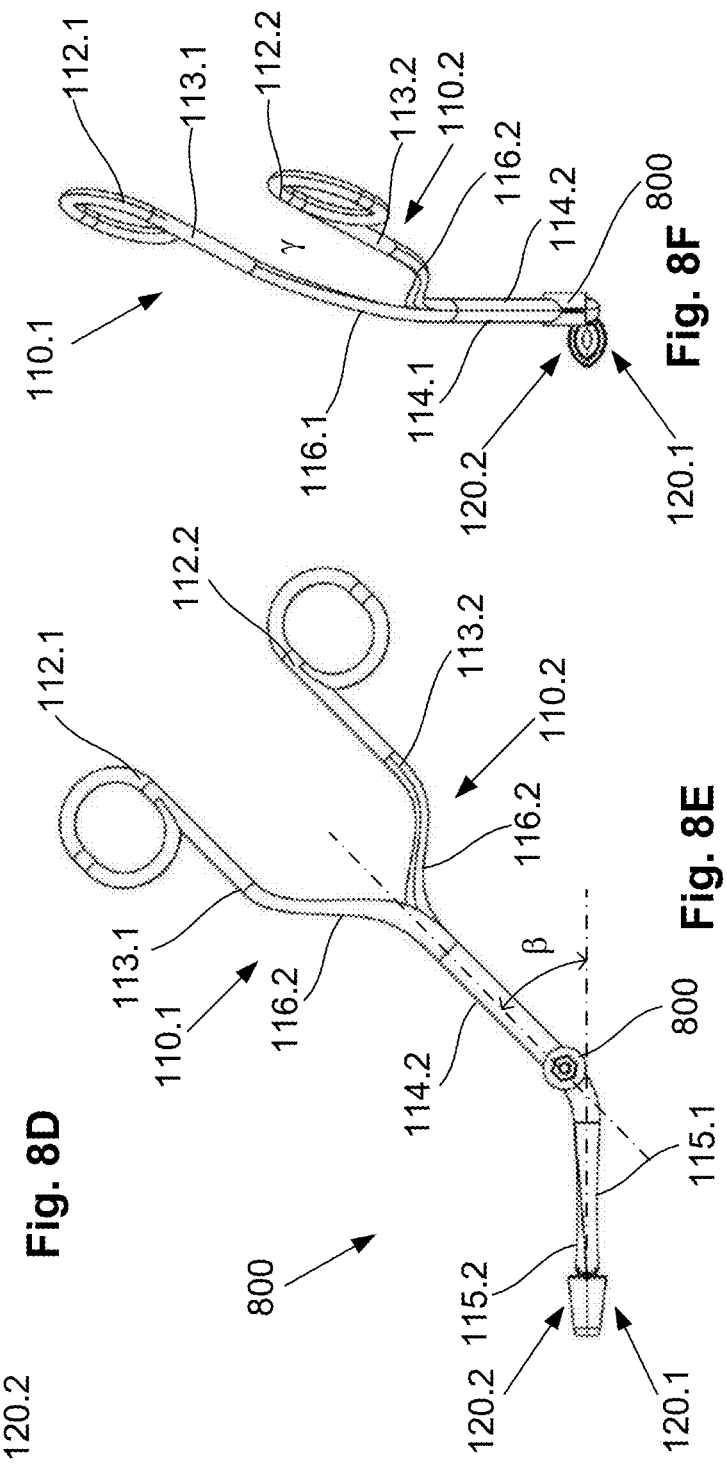

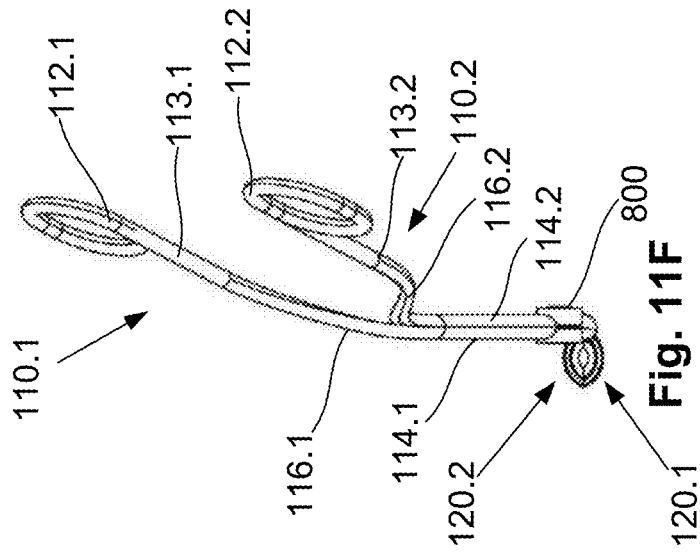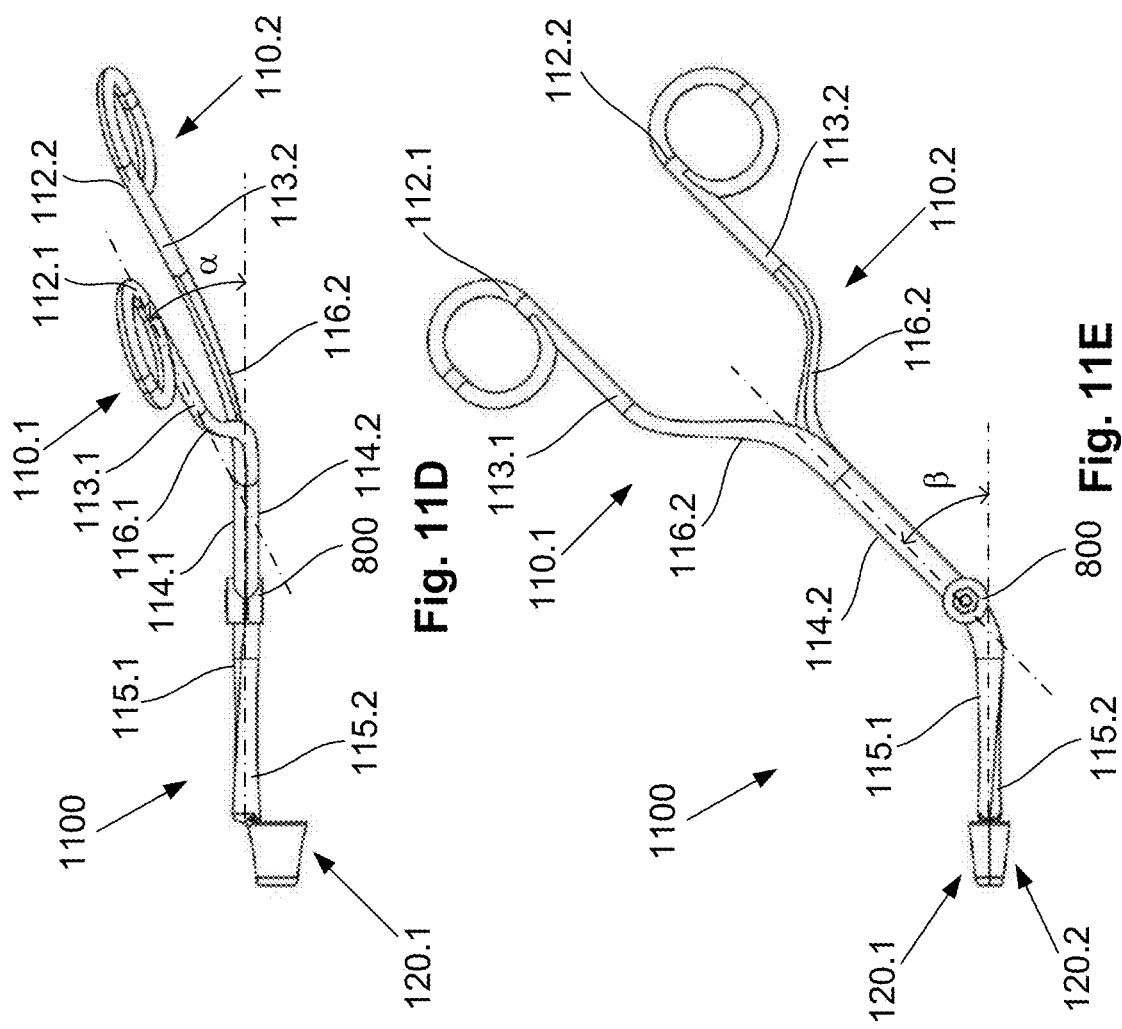

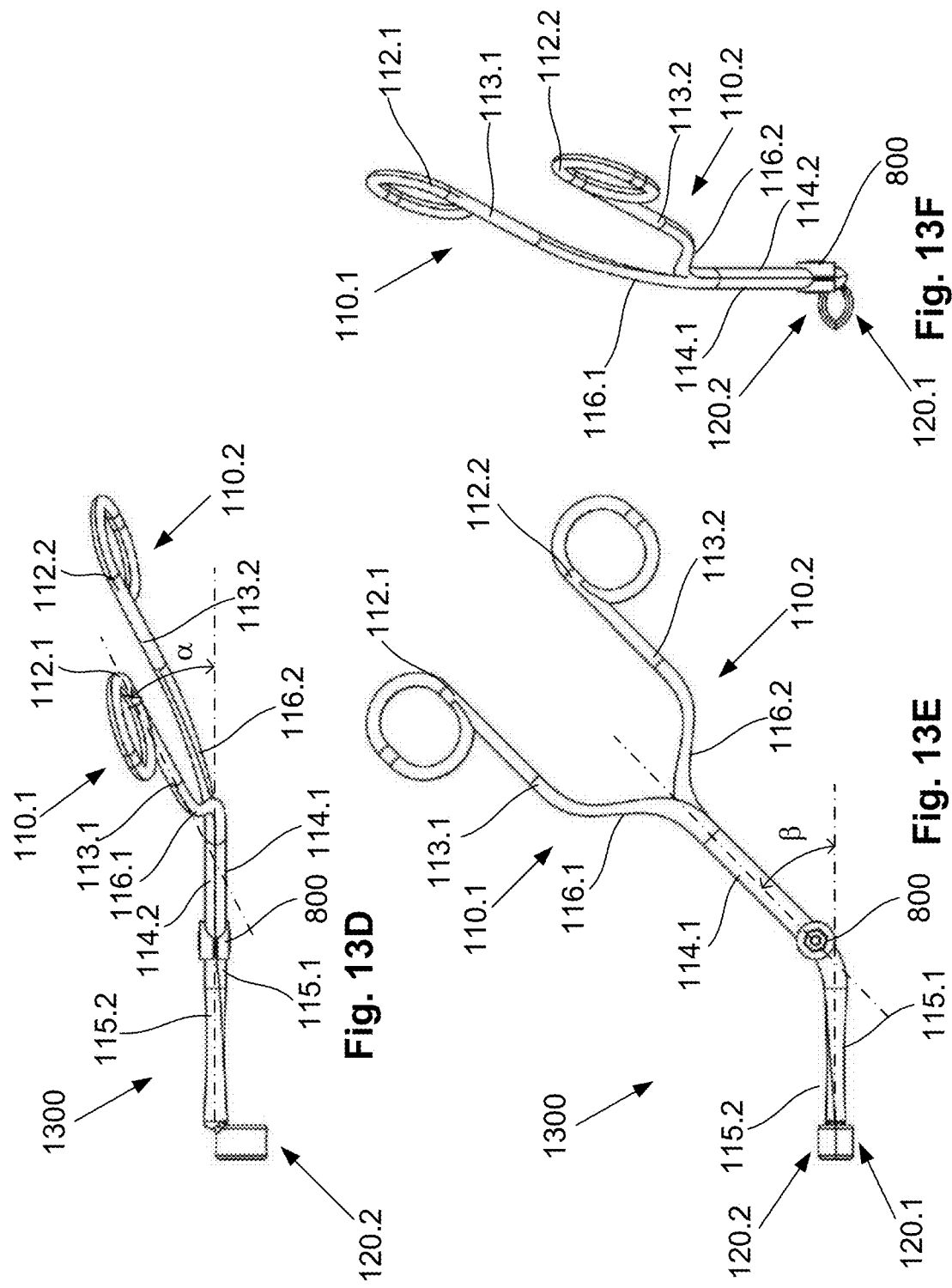

AIRWAY MANIPULATOR DEVICES

BACKGROUND OF THE INVENTION

The present invention relates to devices for insertion into an airway of a subject, particularly for manipulating an anatomical structure or another device in a larynx of the subject, especially for use in an endotracheal intubation procedure.

DESCRIPTION OF THE PRIOR ART

Endotracheal intubation is the procedure through which a medical professional introduces a flexible plastic conduit, an endotracheal tube, generally through the mouth and into the trachea. This allows artificial ventilation, which is required when the breathing ability is compromised by an illness or injury in an emergency situation or is interfered by drug-induced depression during surgery. It is a universal procedure and is performed in the same fashion all over the world.

Every day thousands of intubations are performed by a diverse range of professionals, particularly anaesthetics specialists, intensivists, emergency physicians and pre-hospital medics and paramedics. However endotracheal intubation is a high risk procedure which can lead to death or disability, requires considerable skill and occasionally cannot be accomplished. Even to highly trained professionals, it is often difficult and sometimes unsuccessful. New specialised instruments and advanced techniques are continuously developing with the aim to facilitate this difficult procedure and ensure better success rates.

The aim of the operator is to successfully pass an endotracheal tube through the mouth, pharynx and larynx and into the trachea. The oropharyngeal passage is curved and narrow and ends at the entrance of both the larynx and the oesophagus. The tongue tends to fall back on to the pharynx when a patient is in supine position, the entrance of the larynx can vary in its position due to the particular anatomy of a patient and the epiglottis lies over the entrance of the larynx and usually needs to be moved to expose the glottic opening.

The operator needs to identify the vocal cords at the entrance of the larynx, the epiglottis above the entrance of the larynx in the transversal view with the patient supine, and the oesophagus, below all previous structures on this view. This procedure requires extraordinary skills; it is easier for the endotracheal tube to follow the path towards the oesophagus, it is often difficult to obtain a good view of the larynx, and even with a good view, it is difficult sometimes to introduce the endotracheal tube. Any delay in successfully finalising the procedure is a serious complication, and may potentially be fatal.

The insertion of an endotracheal tube through all these anatomical structures and into the trachea is referred to as endotracheal intubation and typically requires the use of an instrument called laryngoscope which comprises a handle, and a blade. Different shapes of the blade may be used depending on a range of factors such as the age or size of the patient and different procedural options. Laryngoscope blades are generally classified as curved or straight, although a number of styles of curved and straight blades are commercially available. Some styles of blades are designed to be positioned anterior to the epiglottis, and other styles are designed to be positioned posterior to the epiglottis, leading to slightly different movements during the procedure.

During endotracheal intubation, with the patient laying supine, the operator, standing at the top of the head of the patient, introduces the blade of the laryngoscope through the mouth and into the pharynx and manipulates anatomical structures such as the tongue and the epiglottis (depending on the particular patient and type of blade) to expose the entrance of the larynx. Then, under direct visualisation, the operator inserts the tip of the endotracheal tube into the larynx and advances it into the trachea. In the conventional and universal procedure, the operator typically utilises the left hand to hold the laryngoscope by the handle to position the blade and utilises the right hand to carefully introduce the endotracheal tube, pushing it alongside the laryngoscope blade and into the visualised trachea.

Often, because of anatomical variations and challenges, and despite an adequate technique, direct visualisation is difficult. In most of these occasions, adequate visualisation could be obtained by manipulating some of the anatomical structures. Unfortunately, with the conventional laryngoscope and conventional procedure, the operator is utilising both hands and the hand being used to manually introduce the endotracheal tube cannot be used to manipulate anatomical structures to facilitate the procedure. Furthermore, a second operator could not have direct visual access to the entrance of the larynx to help manipulating these structures and will interfere with the vision of the first operator, as the mouth opening, through which the first operator is obtaining the view, is very limited and the operator performing the intubation procedure will usually be in the best viewing position.

Due to the degree of difficulty of the procedure itself, together with the seriousness of the potential complications, this procedure will only be performed by highly skilled professionals. This difficulty and serious complication risk have also meant that the procedure, and the instruments used to perform it, has essentially remained unchanged for decades. The physicians and other professionals who perform endotracheal intubations are unwilling to use new devices or to change the way this is conventionally done, given the difficulties and risks. A new intubation device therefore not only has to offer obvious procedural advantages in comparison to the conventional laryngoscopes, but also has to present similar characteristics in shape and weight and in its method of use, to facilitate adoption by operators already trained and comfortable in the use of conventional laryngoscopes in the often stressful circumstances of performing an intubation procedure.

WO/2016/090435A1 discloses a new intubation device that allows an endotracheal intubation procedure to be performed using a single hand. In particular, the intubation device includes: a laryngoscope blade having a tip and a base; a handle attached to the base of the blade for allowing the intubation device to be held in a hand of a user; a channel for receiving an endotracheal tube, the channel including a blade channel portion extending along the blade substantially from the tip to the base and including an outlet proximate to the tip for allowing a distal end of the endotracheal tube to be advanced from the outlet and a handle channel portion extending partially along the handle from the blade channel portion; and a tube movement mechanism in the handle for moving the endotracheal tube through the channel to thereby advance the endotracheal tube, the tube movement mechanism including a thumb interface for allowing the user to operate the tube movement mechanism using a thumb of the hand that is holding the intubation device, to thereby allow the user to hold the intubation device and advance the endotracheal tube in an endotracheal intubation procedure using a single hand. The entire contents of WO/2016/090435A1 are incorporated herein by reference.

By enabling single handed operation of the intubation device for positioning the blade via the handle and advancing the endotracheal tube, the other hand of the user will remain free for other uses, such as clearing the airway using another device, such as a suction device, or other devices such as forceps or the like to manipulate anatomical structures and/or the endotracheal tube, during the endotracheal intubation procedure as may be required. It would be particularly desirable to manipulate anatomical structures or other devices in the larynx of the subject while the endotracheal intubation procedure is performed. Whilst a number of devices such as forceps have been proposed to assist intubation procedures, these are not suitably configured for manipulating anatomical structures or other devices in the larynx.

Magill Forceps are angled forceps which may be used to guide an endotracheal tube into the larynx or a nasogastric tube into the oesophagus under direct vision. They may also be used to remove foreign bodies from the airway or pharynx. These forceps are primarily used in nasal intubations where the forceps' grip surface is used to grip the tube in the posterior oropharynx and to guide the tube as it is advanced into the lower airway. Since their grip surface is typically serrated, only airway equipment and not tissue should be manipulated with the forceps as significant trauma and bleeding can result. In any event, Magill Forceps do not allow manipulations to be performed proximate to the larynx.

U.S. Pat. No. 7,438,717B2 discloses intubating forceps with a pair of scissor-like arms that are pivotally connected to each other and that continue past the pivot to form a catheter guide. At least two and preferably three bends are disposed in the arms immediately before the pivot, which allow the medical professional to place the guiding end of the forceps in the correct place while maintaining good visual contact with the patient's vocal cords. An alternative embodiment provides a fourth bend near the guiding end of the forceps that allows for easier insertion of a catheter in some patients, such as children.

U.S. Pat. No. 9,364,631B2 discloses further improvements to the above discussed intubating forceps of U.S. Pat. No. 7,438,717B2, and particularly describes forceps having arms pivotally connected for relative movement between an opened position and a closed position include a tube guide formed by arcuate guide portions on each arm. The tube guide includes an inwardly facing arcuate inside wall surface sized for slidable engagement with a tube. The tube guide is fixed at a right angle to the arms and includes a gap formed between tip ends of each of the arcuate guide portions when the arms are in the closed position. Each arm includes a bend fixed at distal ends, wherein the bend is positioned at a distance from the tube guide to form a distal arm portion for each arm permitting an improved view during use of the forceps.

However, the above discussed intubation forceps are particularly adapted for guiding a naso-endotracheal tube and once again do not allow for manipulation of tissue and do not allow manipulations to be performed proximate to the larynx.

Accordingly, there is a need for improved airway manipulator devices which are suitably configured for manipulating anatomical structures or other devices in the larynx, especially when performing an oral endotracheal intubation procedure using a single-handed intubation device.

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

SUMMARY OF THE PRESENT INVENTION

In one broad form an aspect of the present invention seeks to provide a device for insertion into an airway of a subject, the device including: an arm defining a distal end and a proximal end, the arm including: an elongate handle portion at the proximal end, the handle portion extending substantially towards the distal end; and an offset portion located between the distal end and the handle portion, the offset portion being offset dorsally relative to the handle portion and the distal end; and a tip at the distal end of the arm, wherein the arm is configured to allow a user to hold the handle portion outside of a mouth of the subject and move the handle portion to move the tip through the mouth and pharynx of the subject to thereby position the tip proximate to a larynx of the subject.

In one embodiment, the arm includes an elongate insertion portion at the distal end.

In one embodiment, the insertion portion is oriented at an angle relative to the handle portion.

In one embodiment, the angle is an obtuse angle.

In one embodiment, the obtuse angle is at least one of: between 90° and 150°; between 130° and 140°; and about 135°.

In one embodiment, the arm includes an angled portion between the handle portion and the offset portion, the angled portion being oriented at an angle relative to the handle portion.

In one embodiment, the arm includes: a proximal bend between the handle portion and the angled portion; an intermediate bend between the angled portion and the offset portion; and a distal bend between the offset portion and the insertion portion.

In one embodiment, the offset portion includes an elongate section and wherein the handle portion and the elongate section of the offset portion extend along respective frontal planes that are approximately parallel to and offset from one another.

In one embodiment, the distal end and the offset portion extend along a sagittal plane and the handle portion extends laterally outwardly from the sagittal plane.

In one embodiment, the handle portion extends laterally outwardly from the sagittal plane at an angle that is at least one of: between 0° and 90°; between 15° and 45°; between 25° and 30°; and about 27°.

In one embodiment, the tip includes a tip member protruding from the distal end of the arm.

In one embodiment, the tip member protrudes distally and laterally from the distal end.

In one embodiment, the tip member is configured for manipulating an anatomical structure in the larynx.

In one embodiment, the tip member includes an engaging surface.

In one embodiment, the engaging surface is convexly curved.

In one embodiment, the tip member includes an opposing surface that opposes the engaging surface and that is concavely curved.

In one embodiment, the engaging surface is for engaging with a glottis of the subject.

In one embodiment, the engaging surface is for urging a posterior edge of the glottis posteriorly relative to the subject to thereby open the glottis.

In one embodiment, the engaging surface is for engaging with an epiglottic vallecula of the subject.

In one embodiment, the engaging surface is for urging the epiglottic vallecula posteriorly relative to the subject.

In one embodiment, the engaging surface faces dorsally.

In one embodiment, the engaging surface is for urging the epiglottic vallecula anteriorly relative to the subject to thereby open the larynx.

In one embodiment, the engaging surface faces ventrally.

In one embodiment, the tip member is configured for guiding movement of another device inserted into the larynx.

In one embodiment, the tip is configured for guiding movement of at least one of: an endotracheal tube being inserted into the larynx; an endotracheal tube being inserted by another device into the larynx; and a tip of an endotracheal tube being inserted by another device into the larynx.

In one embodiment, the tip member is one of paddle shaped and spoon shaped.

In one embodiment, the tip member includes a notch in a distal edge of the tip member.

In one embodiment, the tip member is laterally tapered.

In one embodiment, the arm defines a first arm of the device and the device further includes a second arm pivotally attached to the first arm at a pivot point located between the tip and the handle portion.

In one embodiment, the second arm defines a distal end and a proximal end, the second arm including: an elongate second handle portion at the proximal end; an second offset portion located between the distal end and the second handle portion, the second offset portion being offset ventrally relative to the second handle portion; and a second at the distal end.

In one embodiment, the respective handle portions of the first arm and the second arm each include a loop for receiving a digit of a hand of a user.

In one embodiment, the pivot point is located between the respective tips and offset portions of the first arm and the second arm.

In one embodiment, the first arm and the second arm are moveable about the pivot point between a closed position and an open position.

In one embodiment, the first arm and the second arm are configured to move from the closed position to the open position when the respective first and second handle portions are one of: urged together; and urged apart.

In one embodiment, when the first arm and the second arm are in the closed position, the respective tips and offset portions of the first arm and the second arm are substantially collocated.

In one embodiment, when the first arm and the second arm are in the closed position, the second handle portion extends substantially parallel to the first handle portion.

In one embodiment, the tip of each arm includes a respective tip member protruding from the distal end of the arm.

In one embodiment, the respective tip members of the first arm and the second arm have opposing shapes.

In one embodiment, when the first arm and the second arm are in the closed position, a passageway is defined between the respective tip members of the first arm and the second arm.

In one embodiment, the passageway defined by the respective tip members of the first arm and the second arm is distally tapered.

In one embodiment, the passageway defined by the respective tip members of the first arm and the second arm is cylindrical.

In one embodiment, the respective tip members of the first arm and the second arm include a textured surface within the cylindrical passageway.

In one embodiment, the respective tip members are configured for engaging anterior and posterior edges of the glottis and opening the glottis by urging the anterior edge anteriorly and posterior edge posteriorly when the first arm and the second arm are moved from the closed position to the open position.

In one embodiment, the arm includes a laterally expanded section extending between the tip and the offset portion.

In one embodiment, the laterally expanded section extends at least partially along the offset portion.

In one embodiment, the laterally expanded section includes a convexly curved surface.

In one embodiment, at least one surface of the laterally expanded section is for engaging with tissue in a pharynx of the subject.

In one embodiment, the arm includes one or more suction ports located proximate to the distal end, the one or more suction ports being in fluid communication with a suction conduit extending at least partially along the arm.

In one embodiment, the arm includes a moveable arm portion at the distal end.

In one embodiment, the device includes a movement interface proximate to the handle for allowing a user to cause the moveable arm portion to move using the movement interface.

In one embodiment, the movement interface is a lever coupled to the handle.

In one broad form an aspect of the present invention seeks to provide a method for use in an endotracheal intubation procedure for delivering an endotracheal tube into a trachea of a subject, the method being performed using: an intubation device including a laryngoscope blade, a handle attached to the blade, and a channel extending at least along the blade and having an outlet proximate to a blade tip that allows a distal end of the endotracheal tube to be advanced from the outlet; and a manipulator device including an arm with a handle portion at a proximal end and a tip at a distal end of the arm; wherein the method includes: a user holding the intubation device by the handle in a first hand and moving the handle to insert the blade of the intubation device into a mouth of the subject so that the blade tip is positioned proximate to a larynx of the subject; the user holding the manipulator device by the handle portion in a second hand and moving the handle portion to: insert the distal end of the arm of the manipulator device into the mouth of the subject adjacent to the blade of the intubation device; and move the tip through the mouth and pharynx of the subject to thereby position the tip proximate to the larynx of the subject; and advancing the endotracheal tube from the outlet of the intubation device while using the manipulator device to at least one of: manipulate an anatomical structure in at least one of the larynx, the pharynx and the mouth; and guide movement of the endotracheal tube.

In one embodiment, the intubation device is a single handed intubation device including a tube movement mechanism that moves the endotracheal tube through the channel to thereby advance the endotracheal tube, the tube movement mechanism including a digit interface that allows the user to operate the tube movement mechanism using a digit of the same hand that is holding the intubation device, wherein the method includes: the user holding the intubation device by the handle and using the digit interface to advance the endotracheal tube into the trachea of the patient using the first hand; and holding the manipulator device by the handle portion using the second hand.

In one embodiment, the tip includes a tip member protruding from the distal end of the arm, the method including using the tip member to urge a posterior edge of the glottis posteriorly relative to the subject to thereby open the glottis.

In one embodiment, the arm defines a first arm of the manipulator device and the tip of the first arm includes a first tip member protruding from the distal end of the first arm, the manipulator device further including a second arm pivotally attached to the first arm at a pivot point located between the tip and the handle portion, the second arm including a second handle portion at a proximal end of the second arm and a second tip member protruding from a distal end of the second arm, the first arm and the second arm being moveable about the pivot point between a closed position and an open position, and wherein the method includes using the first and second tip members to engage anterior and posterior edges of the glottis and open the glottis by urging the anterior edge anteriorly and posterior edge posteriorly when the first arm and the second arm are moved from the closed position to the open position.

In one embodiment, the method includes guiding movement of a tip of the endotracheal tube into the larynx.

In one embodiment, the manipulator device is a device as described above.

It will be appreciated that the broad forms of the invention and their respective features can be used in conjunction, interchangeably and/or independently, and reference to separate broad forms is not intended to be limiting.

BRIEF DESCRIPTION OF THE DRAWINGS

Various examples and embodiments of the present invention will now be described with reference to the accompanying drawings, in which:—

FIGS. 1C to 1E are projection views of the device of FIG. 1A;

FIGS. 3A to 3D are cross section views showing steps for inserting the device of FIG. 1A into the airway of the subject as shown in FIG. 2;

FIGS. 4C to 4E are projection views of the device of FIG. 4A;

FIGS. 6C to 6E are projection views of the device of FIG. 6A;

FIGS. 8D to 8F are projection views of the device of FIG. 8A;

FIGS. 11D to 11F are projection views of the device of FIG. 10A;

FIGS. 13D to 13F are projection views of the device of FIG. 13A;

DETAILED DESCRIPTION OF THE PREFERRED EMBODIMENTS

Figure 1B:
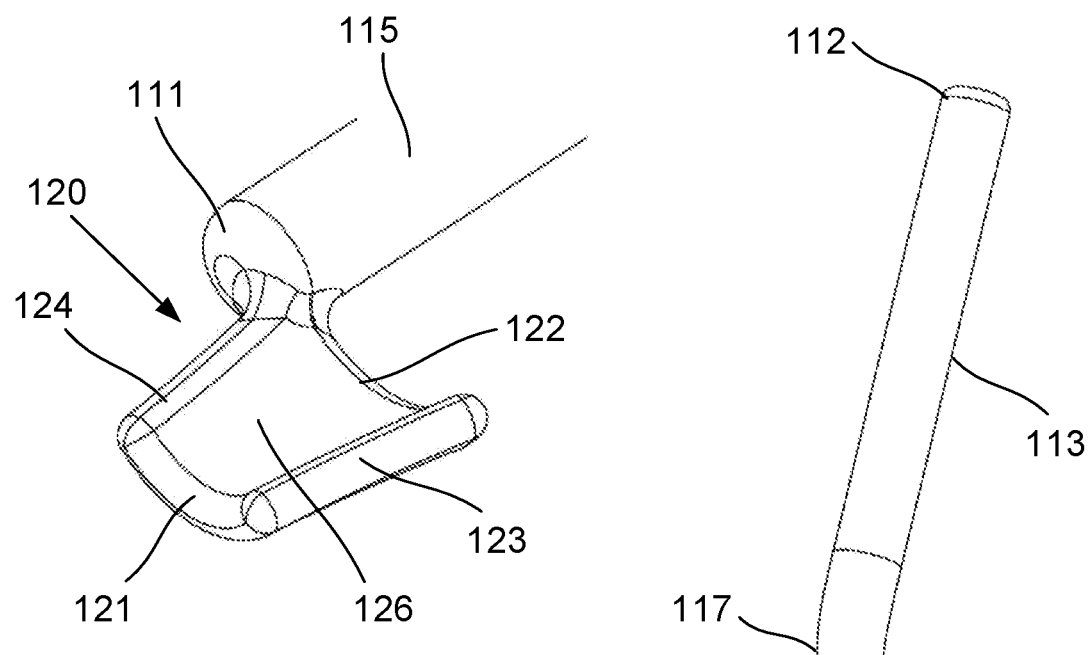
FIG. 1B is a detail view of a tip member of the device of FIG. 1A.
Figure 1A:
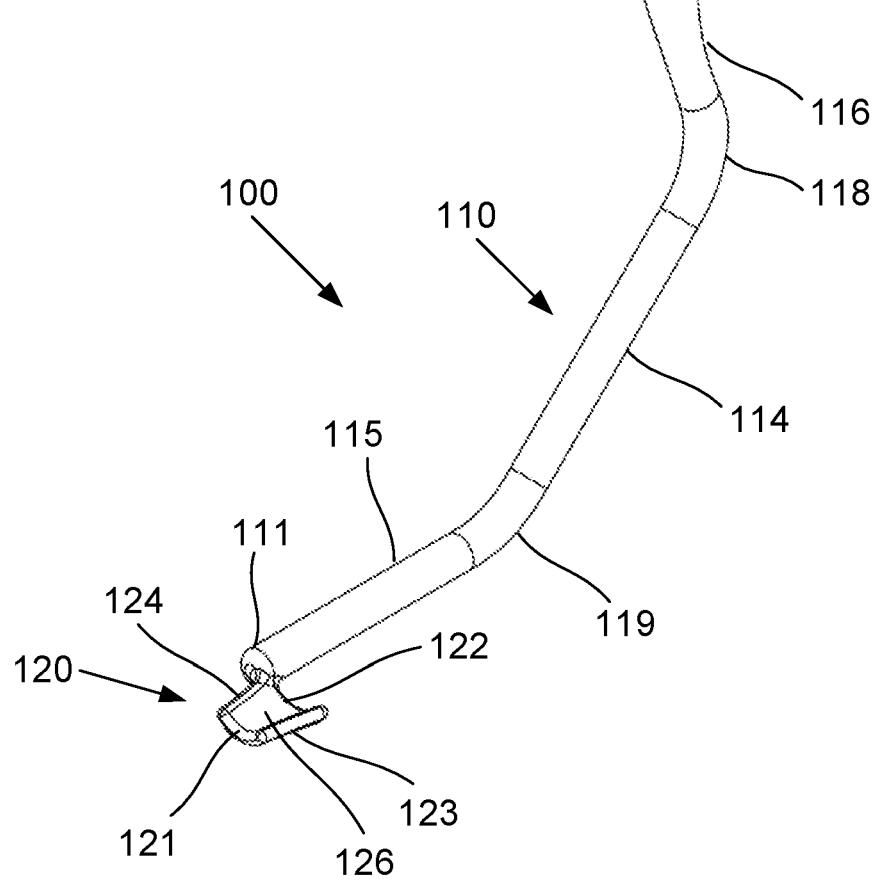
FIG. 1A is a perspective view of a first example of device for insertion into an airway of a subject.

An example of a device 100 for insertion into an airway of a subject 200 will now be described with reference to FIGS. 1A to 1E, which show various views of the device 100, and FIG. 2, which shows the device 100 inserted into the airway of the subject 200 with an intubation device 220 in an endotracheal intubation procedure.

In broad terms, the device 100 includes an arm 110 defining a distal end 111 and a proximal end 112, and a tip 120 at the distal end 111 of the arm 110. The arm 110 includes an elongate handle portion 113 at the proximal end 112. The handle portion 113 extends substantially towards the distal end 111. The arm 110 further includes an offset portion 114 located between the distal end 111 and the handle portion 113. The offset portion 114 is offset dorsally relative to the handle portion 113 and the distal end 111.

Figure 2:
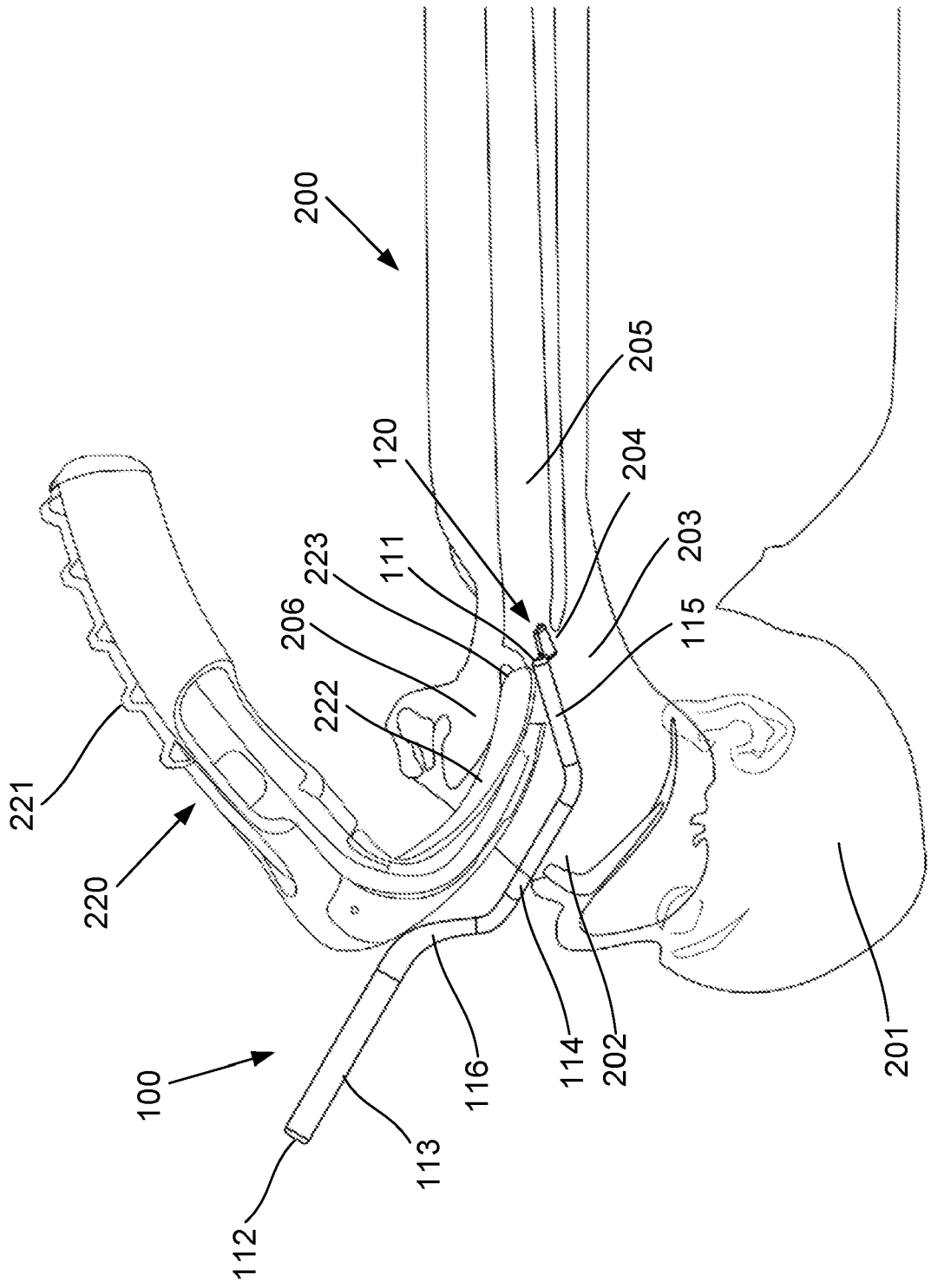
FIG. 2 is a cross section view showing the device of FIG. 1A inserted into an airway of a subject with an intubation device in an endotracheal intubation procedure.
Figure 4B:
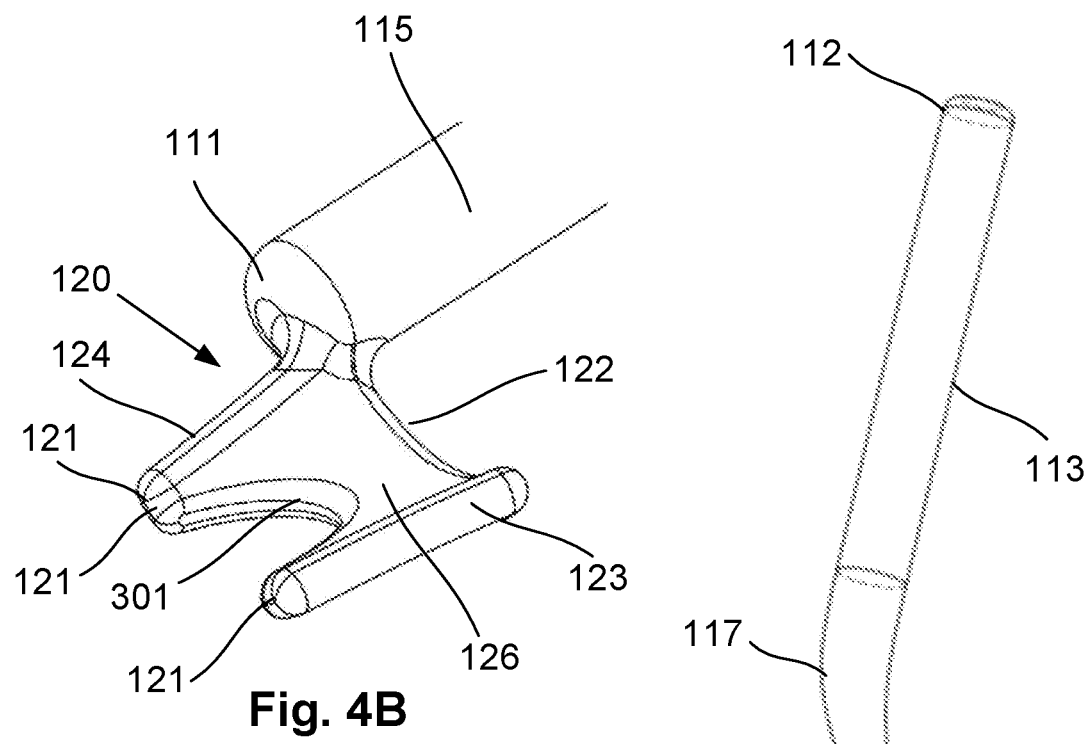
FIG. 4B is a detail view of a tip member of the device of FIG. 4A.
Figure 4A:
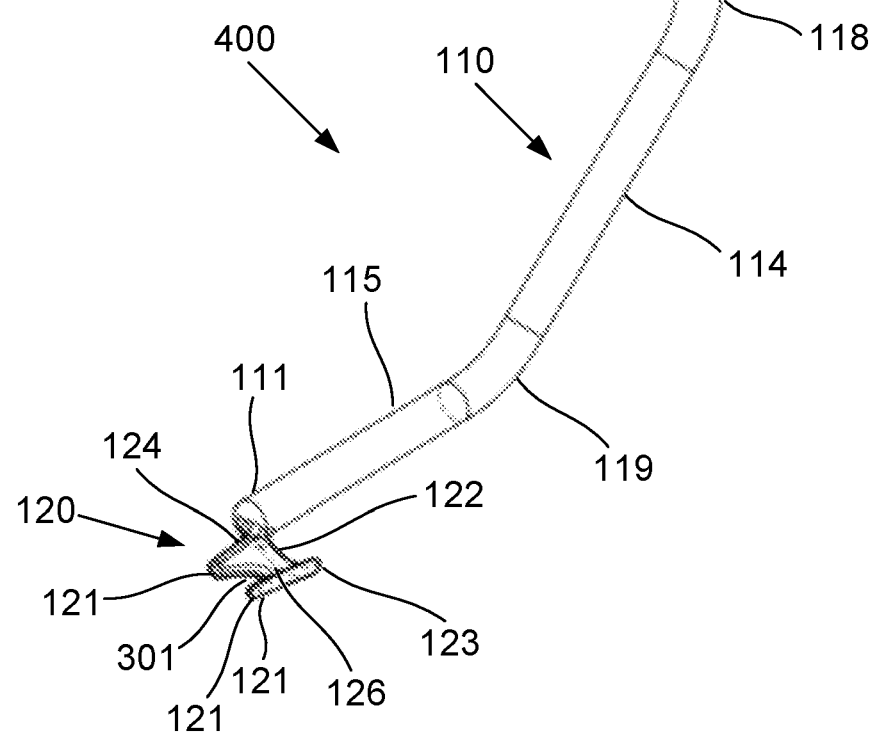
FIG. 4A is a perspective view of a second example of device for insertion into an airway of a subject.

The arm 110 is configured to allow a user to hold the handle portion 113 outside of a mouth of the subject and move the handle portion 113 to move the tip 120 through the mouth 202 and pharynx 203 of the subject 200 to thereby position the tip 120 proximate to a larynx 204 of the subject 200, as shown in FIG. 2.

It is noted that FIG. 2 shows the device 100 inserted into the airway of the subject 200 with an intubation device 220. For the purpose of the following examples, it is assumed that the intubation device 220 is a single handed intubation device as described in WO/2016/090435A1, although it should be appreciated that other forms of intubation devices may be used.

In this example, the intubation device 220 may include a handle portion 221 connected to a blade portion 222 having a distal tip 223. The handle portion 221 allows the user to hold the intubation device 220 and move the blade portion 222 and the distal tip 143 relative to the subject's anatomy. This form of intubation device 220 includes a channel for receiving an endotracheal tube (not shown), and a tube movement mechanism in the handle portion 221 for moving the endotracheal tube through the channel to thereby advance the endotracheal tube. The tube movement mechanism may include a thumb interface for allowing the user to operate the tube movement mechanism using a thumb of the hand that is holding the intubation device, to thereby allow the user to hold the intubation device 220 and advance the endotracheal tube in an endotracheal intubation procedure using a single hand.

Such a single handed intubation device will enable a user to hold and operate the intubation device 220 in one hand, and to hold and operate the device 100 in their other hand. This can allow the user to simultaneously move the tip 120 into a suitable position proximate to a larynx 204 of the subject 200 and advance the endotracheal tube through the larynx 204 to thereby deliver the endotracheal tube into a trachea 205 of the subject. The blade portion 222 of the intubation device 200 may be inserted into the mouth 202 so that the blade portion 222 retains a tongue 206 of the subject and the distal tip 143 is positioned proximate to the larynx 204. The device 100 may also be inserted into the mouth 202 of the subject 200 and moved so that the tip 120 is also positioned proximate to the larynx 204.

Typically, the tip 120 includes a tip member protruding from the distal end 111 of the arm 110, and therefore the terms tip and tip member may be used interchangeably in the following description. However, some embodiments may include a tip 120 having a different configuration of tip member, or no tip member at all, yet still provide similar functionality as discussed herein. Accordingly, it should be appreciated that a tip member is not essential.

As will be discussed in further detail below, the tip member 120 may be configured for different specific uses, but in general the uses will be to manipulate an anatomic structure in the larynx 204, the pharynx 203, or the mouth 202 and/or to guide movement of another device inserted into the larynx 204. In one example, the tip member 120 may be configured for manipulating a glottis of the subject to facilitate advancement of the endotracheal tube past the glottis. In another example, the tip member 120 may be configured for guiding an endotracheal tube during an endotracheal intubation procedure. Specific examples adapted for different uses will be described in due course.

Despite these differing configurations of the tip member (or in some cases the omission of the tip member altogether), the embodiments of the device 100 will generally have similar geometric arrangements, to allow the device 100 to be inserted into the airway of the subject so that the tip 120 can be positioned appropriately in the vicinity of the larynx 204. In particular, embodiments of the device 100 will each be arranged so that the handle portion 113 extends substantially towards the distal end 111, and so that the offset portion 114 located between the distal end 111 and the handle portion 113 is offset dorsally relative to the handle portion 113 and the distal end 111.

It will be appreciated that the handle portion 113 extending towards the distal end 111 will facilitate manual movement of device 100 to position the tip 120 (which may include a tip member of a desired configuration that protrudes from the distal end 111) in a desired position, whilst the offset portion 114 is offset relative to the handle portion 113 and the distal end 112 so that this can help to avoid interference with the blade portion 222 of the intubation device 220 and anatomical structures located directly between the mouth 202 and the larynx 204 in use.

Accordingly, the geometric arrangement of the device 100 can facilitate manipulation of anatomical structures or guiding other devices in the vicinity of the larynx 204 during an endotracheal intubation procedure whilst the offset portion 114 helps to reduce the impact on the subject's other anatomical structures away from the larynx and the intubation device 220 being used to deliver the endotracheal tube.

Whilst the offset portion 114 is depicted as an elongate section of the arm 110 in this example, it should be appreciated that this is not essential and the offset portion 114 may have a different shape compared to that depicted in this example, such as a curved shape, provided that there is a section of the arm 110 that is offset from the handle portion 113 and the distal end 111 to thereby help to avoid interference with the intubation device 220 and anatomical structures located between the mouth 202 and the larynx 204 in use, as mentioned above.

Further optional features of the device 100 will now be described.

The arm 110 may include an elongate insertion portion 115 at the distal end 111. The insertion portion may provide a substantially straight section of the arm leading towards the distal end 111 and tip member 120 protruding therefrom.

The insertion portion 115 may be oriented at an angle β relative to the handle portion 113. This angle β will typically be an obtuse angle, which may be selected with regard to the anatomical structures of the subject's mouth and pharynx 203, and/or the particular design of the intubation device 220. In some examples, the angle may be between 90° and 150°, or more preferably the angle β may be between 130° and 140°, and in one particular preferred embodiment the angle β may be about 135°.

The arm 110 may also include an angled portion 116 between the handle portion 113 and the offset portion 114. The angled portion 116 may also be oriented at an angle relative to the handle portion 114. This angled portion 116 will serve to transition between the geometries of the handle portion 113 and the offset portion 114.

The arm 110 may further include bends between its different portions, such as a proximal bend 117 between the handle portion 113 and the angled portion 116, an intermediate bend 118 between the angled portion 116 and the offset portion 114, and a distal bend 119 between the offset portion 114 and the insertion portion 115.

As depicted in this example, the offset portion 114 may include an elongate section. Whilst this is not essential as mentioned above, in embodiments such as this, the handle portion 113 and the elongate section of the offset portion 114 may extend along respective frontal planes that are approximately parallel to and offset from one another. This parallel and offset relationship can be best observed in FIG. 1D which is a side view oriented perpendicularly to the aforementioned frontal planes.

The distal end 111 and the offset portion 114 may extend along a sagittal plane and the handle portion 114 may extends laterally outwardly from the sagittal plane. This relationship can be best observed in FIG. 1C which is a plan view oriented perpendicularly to the sagittal plane that is aligned with the distal end 111 and the offset portion 114.

The handle portion 113 may extend laterally outwardly from the sagittal plane at an angle α. In some examples, the angle α may be between 0° and 90°, but preferably the angle α may be between 15° and 45°, or more preferably the angle α may be between 25° and 30°, and in one particular preferred embodiment the angle α may be about 27°.

The above discussed planar and angular relationships between different portions of the device 100 may be selected to ensure that the device is both suitable for use with the subject's anatomy and/or to provide improved ergonomics for the user.

The tip member 120 will typically protrude distally and laterally from the distal end 111, although the particular configuration of the tip member 120 will depend on its intended use, which, as mentioned above, may vary. The tip member includes a distal edge 121 and an opposing proximal edge 122, and lateral edges 123, 124.

The tip member 120 may be particularly configured for manipulating an anatomical structure in the larynx 204. The tip member 120 may include an engaging surface 125. This engaging surface 125 may be convexly curved as shown, where the curved surface may allow for engagement with the anatomical structure with a reduced chance of inflammation or damage. The tip member 120 may also include an opposing surface 126 that opposes the engaging surface 125 and that is concavely curved. The curvature of the opposing surface 126 may allow the tip member 120 to also guide an endotracheal tube into the trachea and thus may be selected depending on the particular tube geometry.

In the example of FIGS. 1A to 1E, the engaging surface 125 is specifically for engaging with a glottis of the subject 200. In particular, the engaging surface is for urging a posterior edge of the glottis posteriorly relative to the subject 200 to thereby open the glottis. Opening the glottis in this manner can facilitate improved insertion of the tip of the endotracheal tube through the glottis.

The tip member 120 may be defined as paddle shaped or spoon shaped. The tip member 120 may also be laterally tapered as shown, which can assist with the insertion of the tip member 120 into the glottis and its engagement with the edge of the glottis.

However, as mentioned above, a tip member 120 is not necessary in all cases, and in some embodiments the tip 120 of the device may coincide with its distal end 111, with other features of the device being configured for manipulating anatomical structures of the subject 200 or guiding other devices, as will be discussed in further detail in due course.

An example process for inserting the device 100 will now be discussed with regard to FIGS. 3A to 3D. The process assumes the intubation device 220 has already been put into position as part of the intubation procedure, with the blade portion 222 inserted into the mouth 202 and its distal tip 223 located near the larynx 204, as shown in FIG. 3A. Then, the device 100 can be initially inserted as shown in FIG. 3B, by passing the tip member 120 though the mouth 202 and moving it towards the pharynx 203. The user may move the arm 110 in an arc so that the tip member 120 can move through the pharynx 203 yet without interference or trauma due to contact of the other parts of the device 100 with the subject's anatomy. The tip member 120 will come into proximity of the larynx 204 as shown in FIG. 3C. Once the tip member is in position, the device 100 can be moved to cause the above mentioned engaging surface 125 to engage with the posterior edge of the glottis and urge it posteriorly relative to the subject 200 (in other words, pushing down) to thereby open the glottis, as shown in FIG. 3D.

A second example of the device 400 will now be described with reference to FIGS. 4A to 4E. This version of the device 400 shares its overall geometric arrangement with the previous example and therefore features corresponding to those in the previous example have been assigned the same reference numerals.

Figure 5:
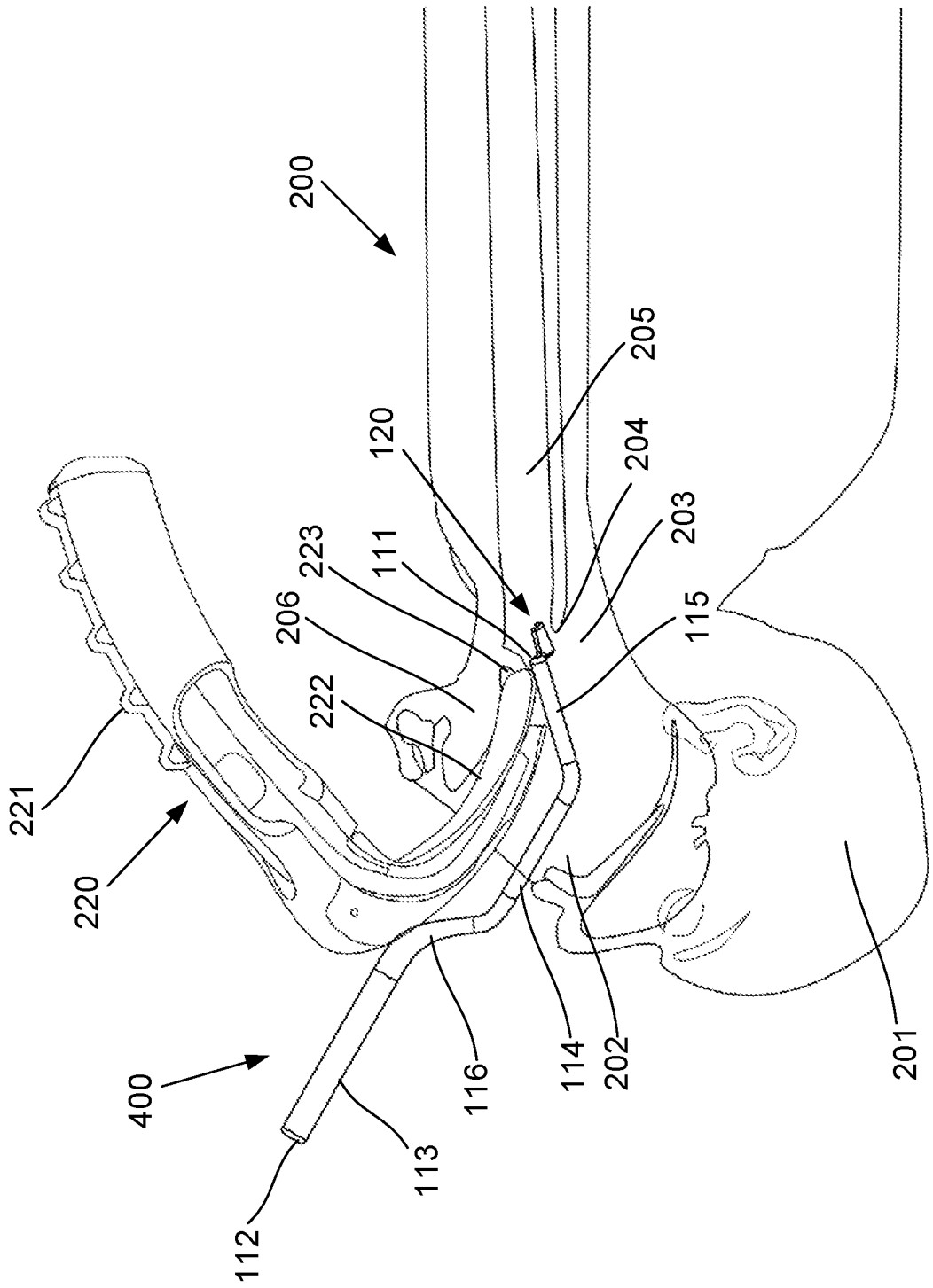
FIG. 5 is a cross section view showing the device of FIG. 4A inserted into an airway of a subject with an intubation device in an endotracheal intubation procedure.
Figure 6B:
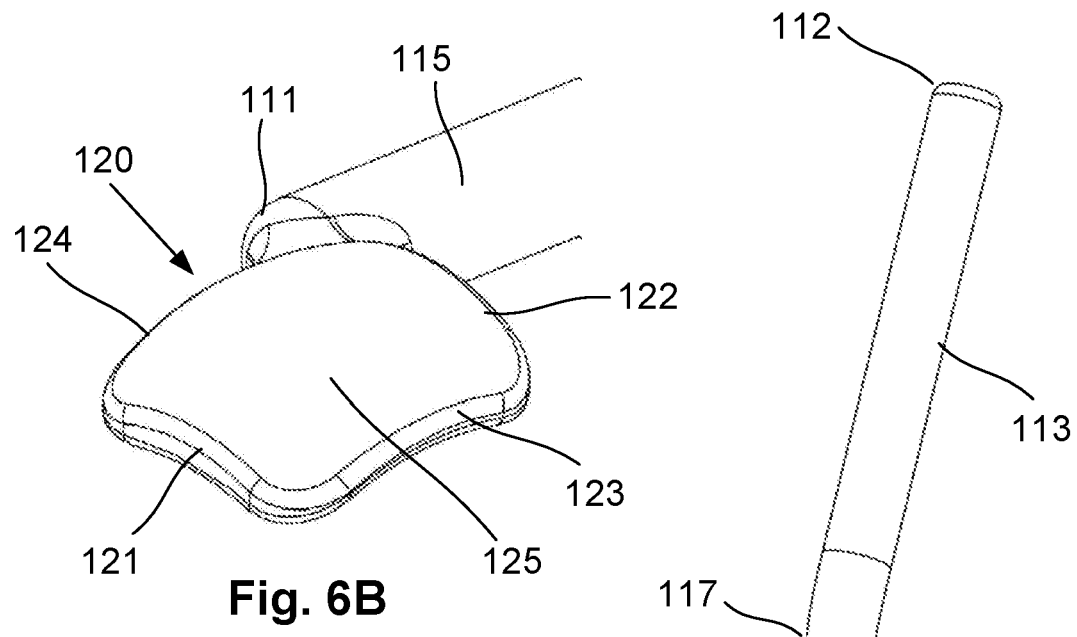
FIG. 6B is a detail view of a tip member of the device of FIG. 6A.
Figure 6A:
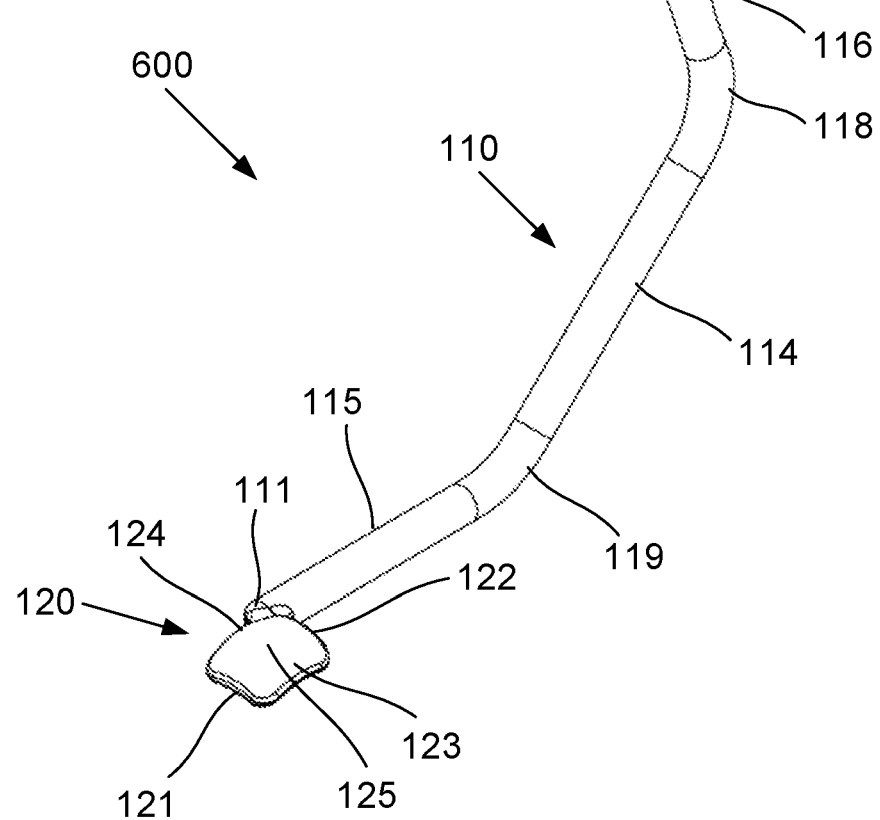
FIG. 6A is a perspective view of a third example of device for insertion into an airway of a subject.

However, the design of this device 400 differs with regard to the particular arrangement of the tip member 120. The tip member 120 is also for engaging with a glottis of the subject 200, and specifically urging a posterior edge of the glottis posteriorly relative to the subject 200 (in other words, pushing down) to thereby open the glottis as shown in FIG. 5, similar to the previous example. In this case the tip member 120 includes a notch 301 in the distal edge 121 of the tip member 120. This notched arrangement can help to maintain separation of the vocal chords as the engaging surface 125 is used to engage the glottis.

Whilst the particular configuration of the tip member 120 is different in this example, the configuration of the handle 110 may be essentially the same as for the previous example.

A third example of the device 600 will now be described with reference to FIGS. 6A to 6E. Once again, this version of the device 600 shares its overall geometric arrangement with the previous examples and therefore features corresponding to those in the previous examples have been assigned the same reference numerals.

Figure 7:
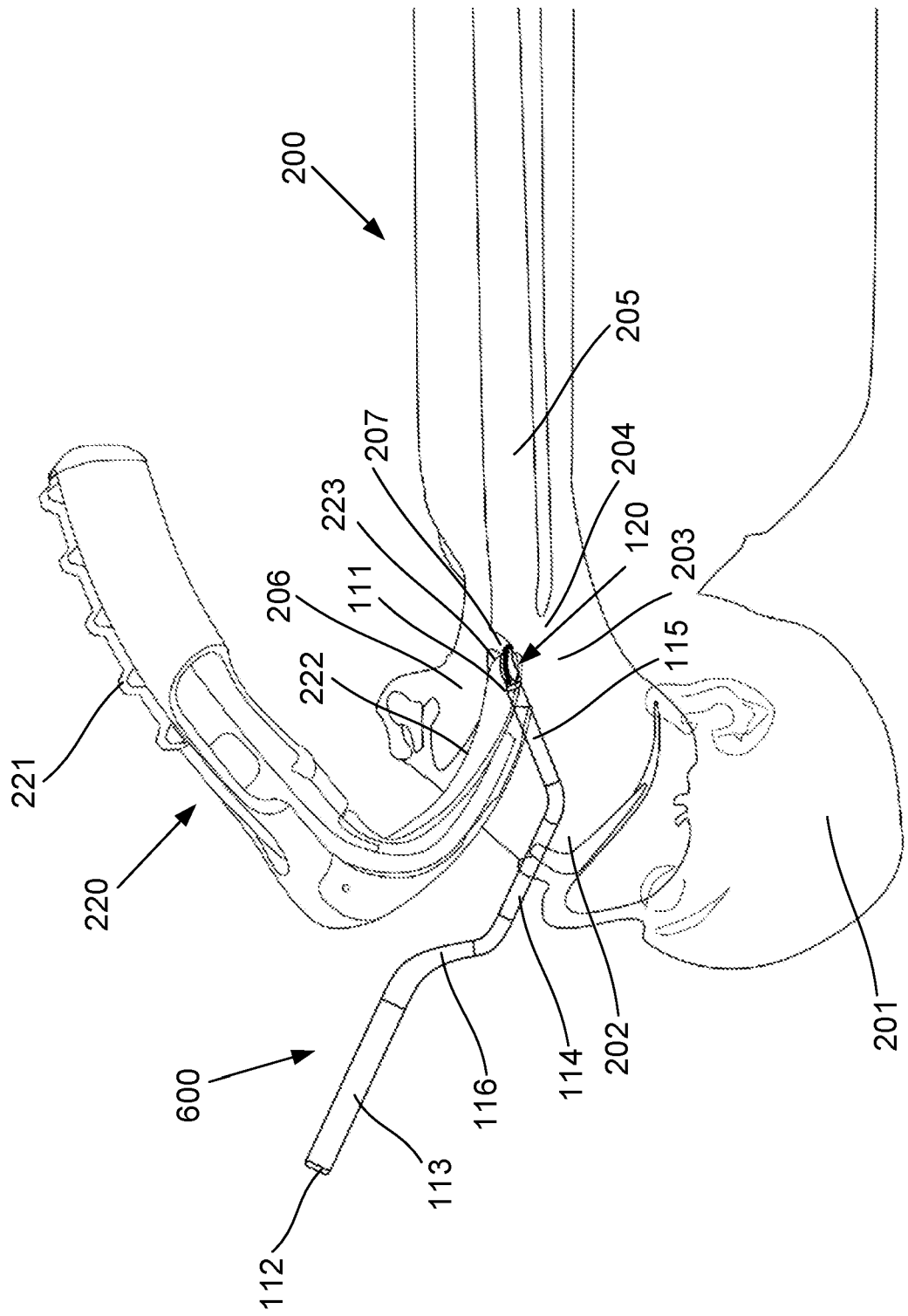
FIG. 7 is a cross section view showing the device of FIG. 6A inserted into an airway of a subject with an intubation device in an endotracheal intubation procedure.
Figure 8A:
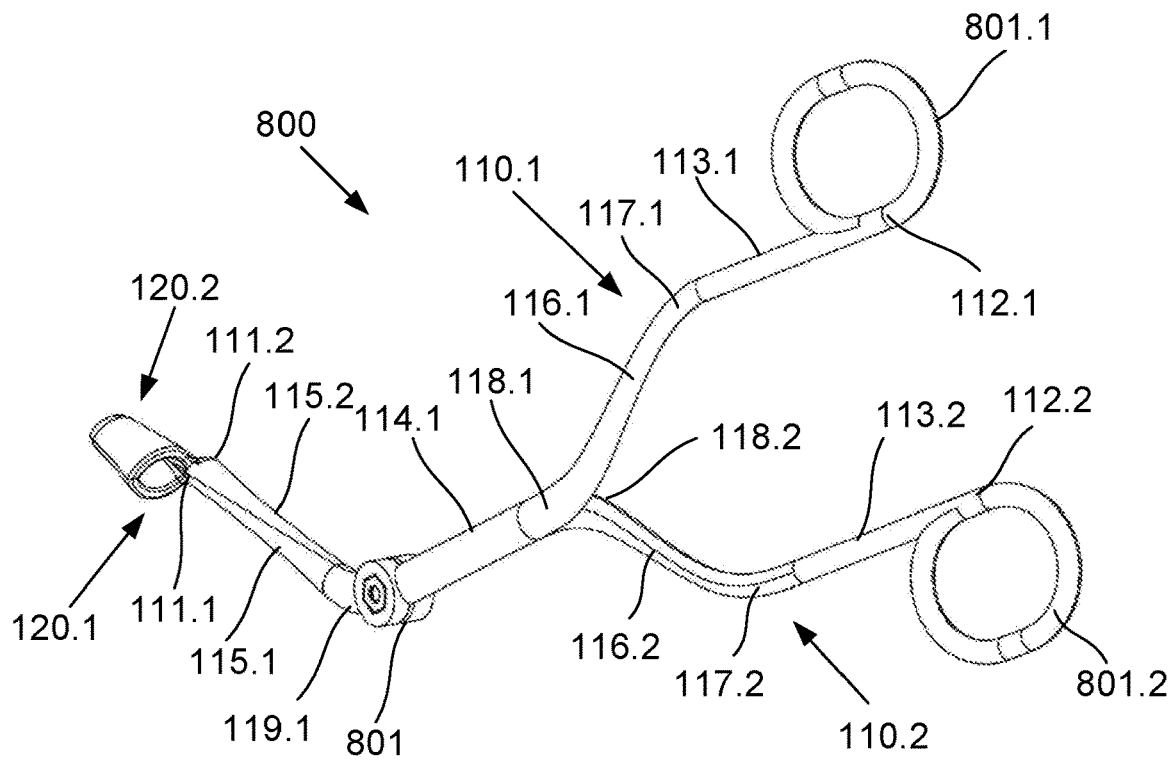
FIG. 8A is a perspective view of a fourth example of device for insertion into an airway of a subject, the device being in a closed position.
Figure 8B:
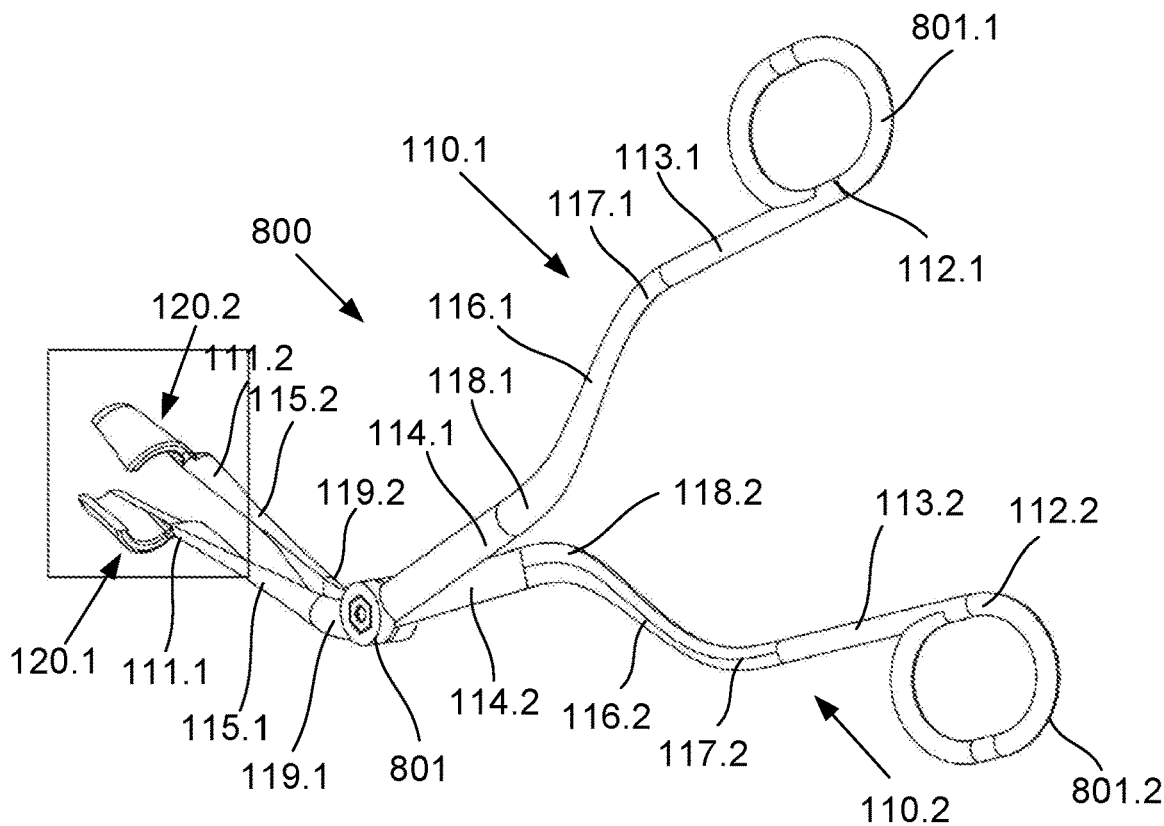
FIG. 8B is a perspective view of the device of FIG. 8A, the device being in an open position.
Figure 8C:
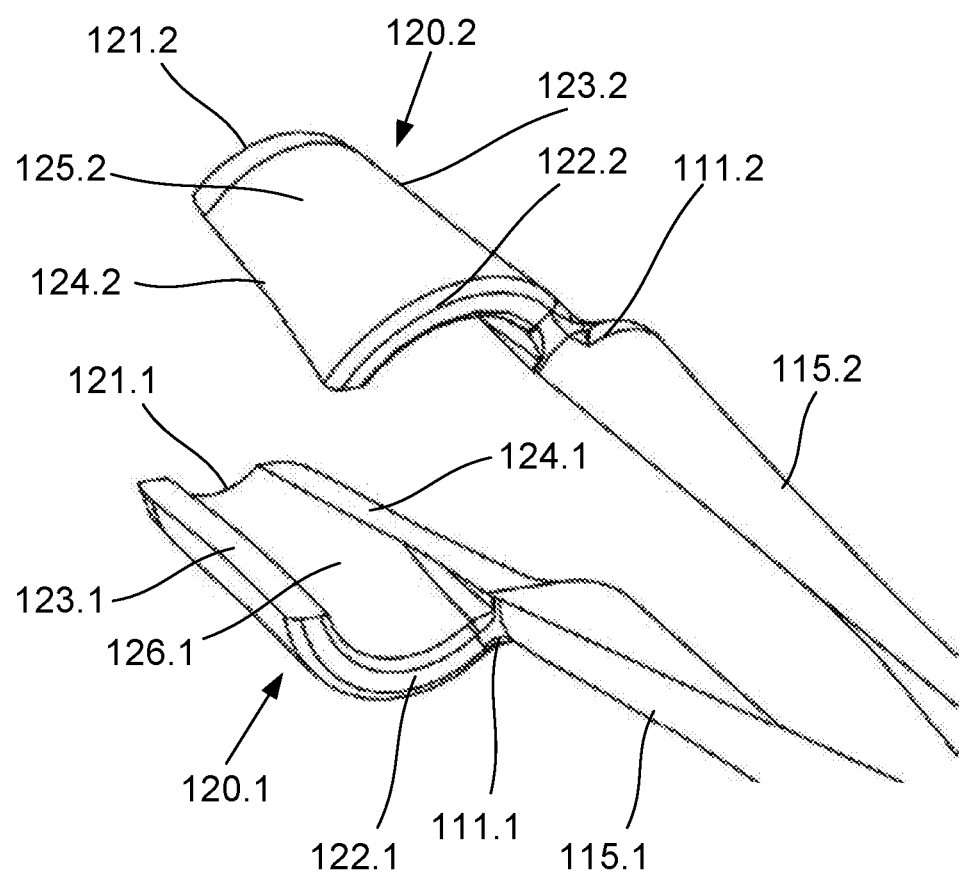
FIG. 8C is a detail view of tip members of the device of FIG. 8A.

In this case, the tip member 120 is configured so that the engaging surface 125 is for engaging with an epiglottic vallecula 207 of the subject 200. In this particular example, the engaging surface 125 is for urging the epiglottic vallecula anteriorly relative to the subject 200 (in other words, lifting forwards) to thereby open the larynx 204 as shown in FIG. 7. It will be noted that the engaging surface 125 faces ventrally in this embodiment (with regard to the position of the device 600 relative to the subject in use), since the tip member 120 is configured to urge an anatomical structure anteriorly. This can be contrasted with the configurations of the tip member 120 in the two earlier examples where the engaging surface 125 faces dorsally (with regard to the position of the device 100, 400 relative to the subject in use), since the tip members 120 in those versions are configured to urge an anatomical structure posteriorly.

However, in some other examples, the engaging surface 125 may be configured for urging the epiglottic vallecula 207 posteriorly relative to the subject 200 (in other words, pushing down) to thereby manipulate the larynx in a different manner. For instance, the engaging surface 125 may be used to effectively move the larynx 204 posteriorly relative to the subject 200. In such cases, the engaging surface may face dorsally as per the earlier described embodiments.

In any event, it is noted that the tip member 120 in the third example of the device 600 has a broader and more prominently curved shape compared to the earlier examples of the device 100, 400. This different shape has been selected to better conform to the shape of the epiglottic vallecula 207, which the tip member 120 is intended to manipulate, compared to the earlier examples of the device 100, 400, where the respective tip members 120 are intended to manipulate the glottis.

As mentioned above, the tip member 120 may additionally or alternatively be configured for guiding movement of another device inserted into the larynx 204. For example, the tip may be configured for guiding movement of an endotracheal tube being inserted into the larynx 204, an endotracheal tube being inserted by another device into the larynx 204, or a tip of an endotracheal tube being inserted by another device into the larynx 204. It should be appreciated that any of the previous examples of the device may be used for guiding an endotracheal tube or other inserted device, in addition to their functionality for manipulating an anatomical structure proximate to the larynx 204. However, some embodiments of the device may be more specifically configured for use as a guide, and some embodiments may not be intended to manipulate any anatomical structures at all.

Whilst the three example devices 100, 400, 600 described so far include a single arm, embodiments of the device may include two arms provided in an arrangement similar to forceps.

Accordingly, a fourth example of a device 800 with two arms 110.1, 110.2 will now be described with reference to FIGS. 8A to 8F.

The device 800 includes a first arm 110.1 which generally corresponds to the arm 110 of the previous examples, and further includes a second arm 110.2 pivotally attached to the first arm 110.1 at a pivot point 801 located between the tip 111.1 and the handle portion 113.1 of the first arm 110.1.

The second arm 110.2 shares a number of similar features with the first arm 110.1 and these similar features have been assigned similar reference numerals, whereby features belonging to the first arm 110.1 are denoted by a suffix of "0.1" and features belonging to the first arm 110.1 are denoted by a suffix of "0.2".

The second arm 110.2 defines a distal end 112.2 and a proximal end 111.2. In particular, the second arm 110.2 also includes an elongate second handle portion 113.2 at the proximal end 112.2, an second offset portion 114.2 located between the distal end 111.2 and the second handle portion 113.2, and a second tip member 120.2 protruding from the distal end 111.2. However, in the case of the second arm 110.2, the second offset portion 114.2 is offset ventrally relative to the second handle portion 113.2. This can be contrasted with the first offset portion 114.1 of the first arm 110.1 which is offset dorsally relative to both the first handle portion 113.1 and the distal end 111.1. The opposing offset directions effectively result in the second handle portion 113.2 being offset away from the first handle portion 113.1 as shown in FIGS. 8A to 8F, hence defining pivotally connected arms 110.1, 11.2 that function in the manner of forceps.

The pivot point 801 may be located between the respective tips 111.1, 111.2 and offset portions 114.1, 114.2 of the first arm 110.1 and the second arm 110.2. As seen in FIGS. 8A to 8F, the pivot point may be located on or near the distal bend 119.1, 119.2 between the respective insertion portions 115.1, 115.2 and offset portions 114.1, 114.2.

The respective tip members 120.1, 120.2 of the first arm 110.1 and the second arm 110.2 may have opposing shapes, as shown in this example. It will be appreciated that the tip members 120.1, 120.2 in this example have similar configurations as the tip member of the first example of the device 100, but with each of the respective tip members 120.1, 120.2 having their engaging surface 125.1, 125.2 facing in opposing directions.

The first arm 110.1 and the second arm 110.2 are typically moveable about the pivot point 801 between a closed position and an open position. In the open position, the tip members 120.1, 120.2 will typically be moved apart from one another. The first arm 110.1 and the second arm 110.2 are configured to move from the closed position to the open position when the respective first and second handle portions 113.1, 113.2 are urged together or urged apart, depending on the particular design of the device.

The device 800 of FIGS. 8A to 8F provides an example in which the first arm 110.1 and the second arm 110.2 are moved into the open position by urging the handle portions 113.1, 113.2 apart. On the other hand, FIGS. 11A to 11F show a fifth example of a device 1100, in which the first arm 110.1 and the second arm 110.2 are moved into the open position by urging the handle portions 113.1, 113.2 together. It will be noted that the arrangement of the tip members 120.1, 120.2 relative to the arms 110.1, 110.2 is reversed in the device 1110 compared to the device 800. This allows the tip members 120.1, 120.2 of the device 1100 to be move apart from one another when the handle portions 113.1, 113.2 are urged together rather than apart in the device 800.

In any event, when the first arm 110.1 and the second arm 110.2 are in the closed position, the respective tips 111.1, 111.2 and offset portions 114.1, 114.2 of the first arm 110.1 and the second arm 110.2 may be substantially collocated as shown in either example. When the first arm 110.1 and the second arm 110.2 are in the closed position, the second handle portion 113.2 may extend substantially parallel to the first handle portion 113.1. This parallel configuration represents a convenient gripping arrangement for the user's hand.

Furthermore, the respective handle portions 113.1, 113.2 of the first arm 110.1 and the second arm 110.2 may each include a loop 801.1, 801.2 for receiving a digit of the hand of a user. It will be appreciated that the loops 801.1, 801.2 may facilitate single handed operation of the device 800.

When the first arm 110.1 and the second arm 110.2 are in the closed position, a passageway may be defined between the respective tip members 120.1, 120.2 of the first arm 110.1 and the second aim 110.2. This passageway defined by the respective tip members 120.1, 120.2 of the first arm 110.1 and the second arm 110.2 may be distally tapered as shown in the examples of FIGS. 8A to 8F and 11A to 11F.

The respective tip members 120.1, 120.2 of the device 800 may be configured for engaging anterior and posterior edges of the glottis and opening the glottis by urging of the anterior edge anteriorly and posterior edge posteriorly when the first arm 110.1 and the second arm 110.2 are moved from the closed position to the open position.

Figure 9:
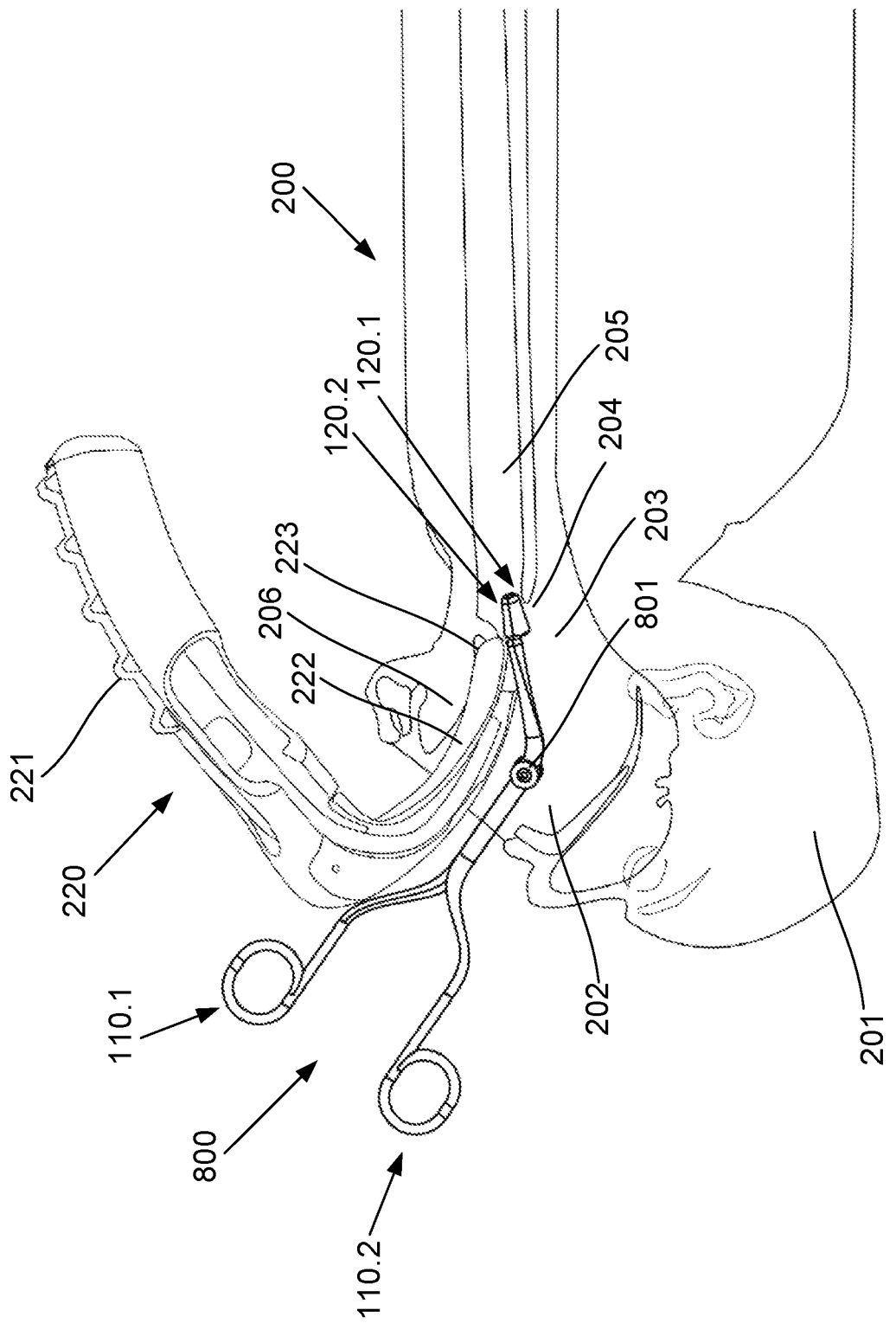
FIG. 9 is a cross section view showing the device of FIG. 8A inserted into an airway of a subject with an intubation device in an endotracheal intubation procedure.

The inserted position of the device 800 can be seen in FIG. 9, where the tip members 120.1, 120.2 are positioned proximate to the larynx and particularly in the glottis.

Figure 10A:
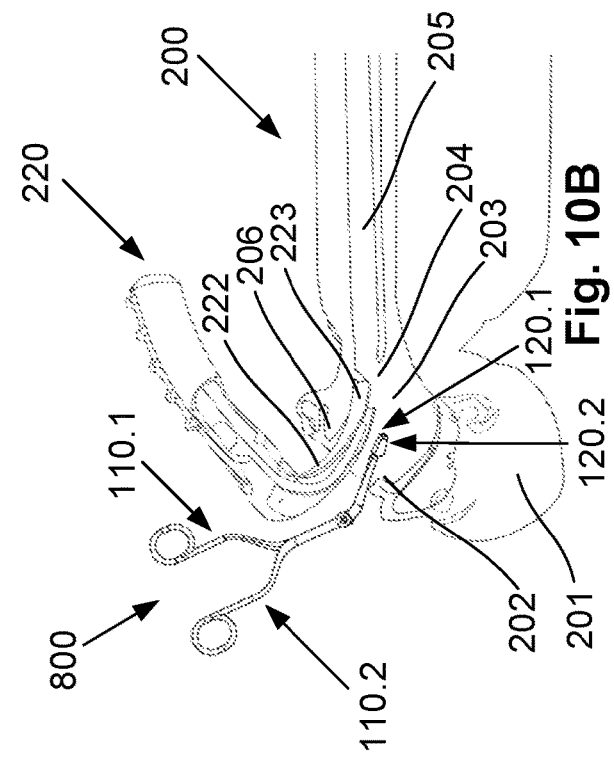
FIGS. 10A to 10D are cross section views showing steps for inserting the device of FIG. 8A into the airway of the subject as shown in FIG. 2.
Figure 10B:
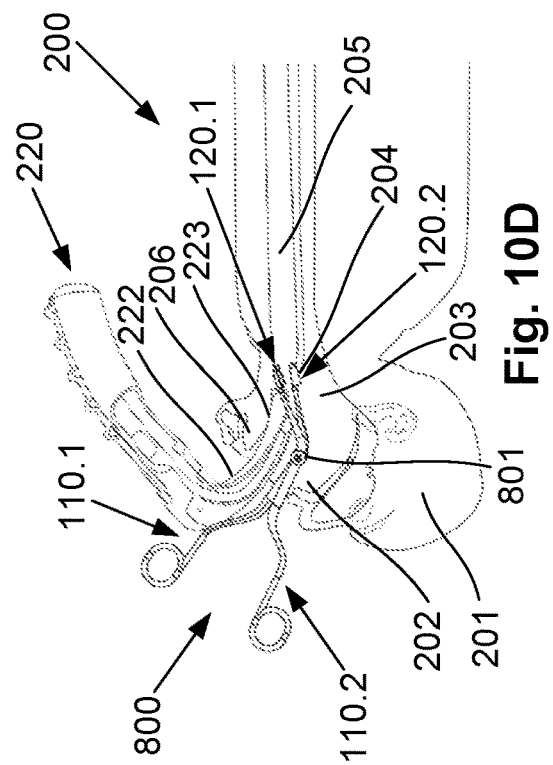
Figure 10C:
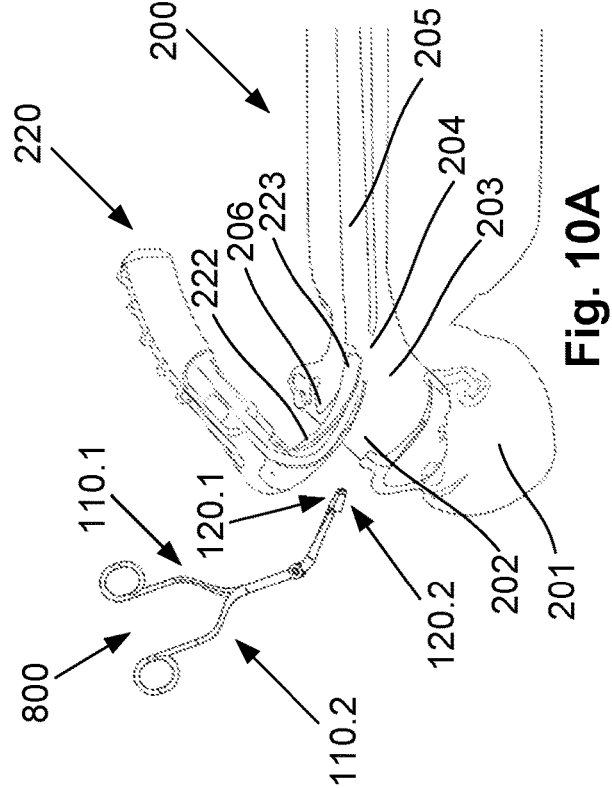
Figure 10D:
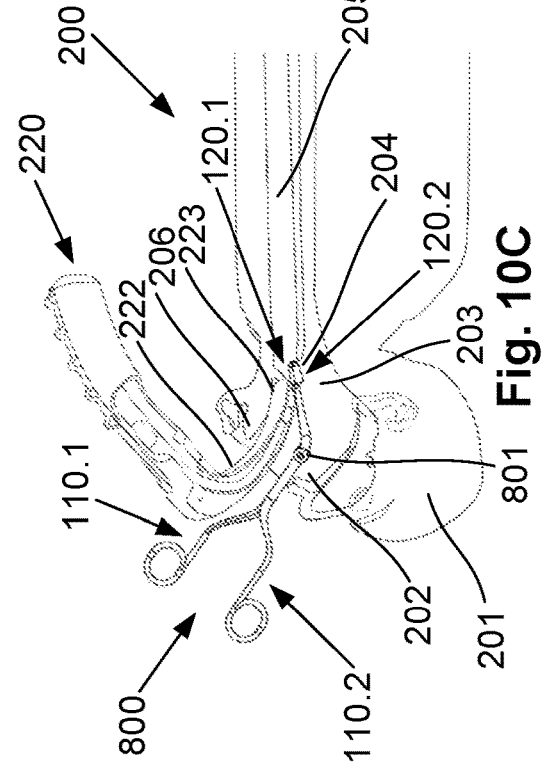
Figure 11A:
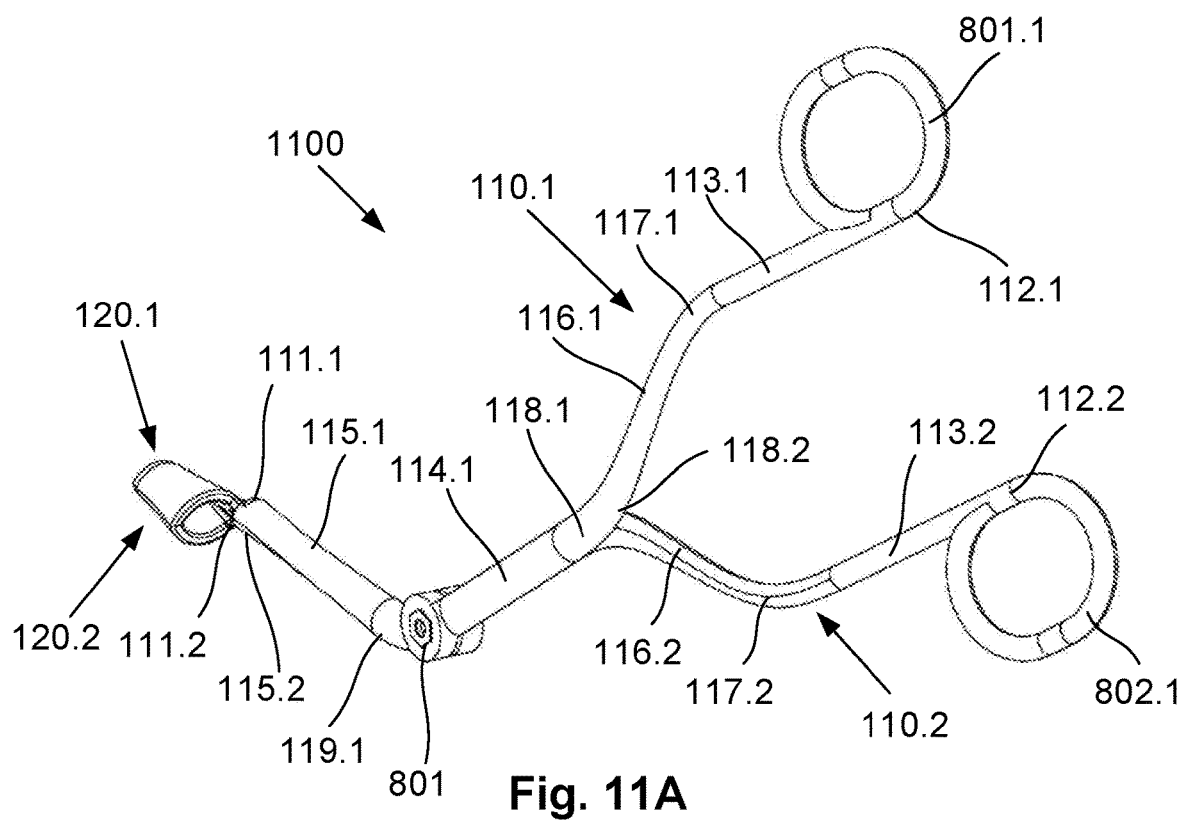
FIG. 11A is a perspective view of a fifth example of device for insertion into an airway of a subject, the device being in a closed position.
Figure 11B:
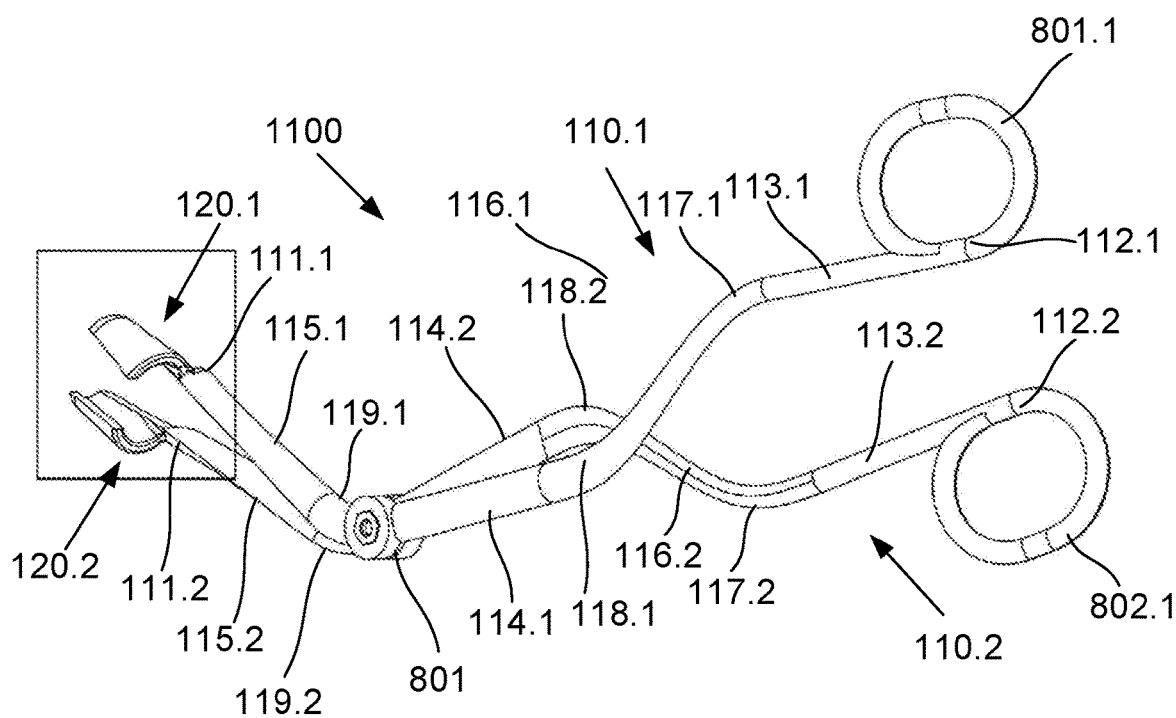
FIG. 11B is a perspective view of the device of FIG. 11A, the device being in an open position.
Figure 11C:
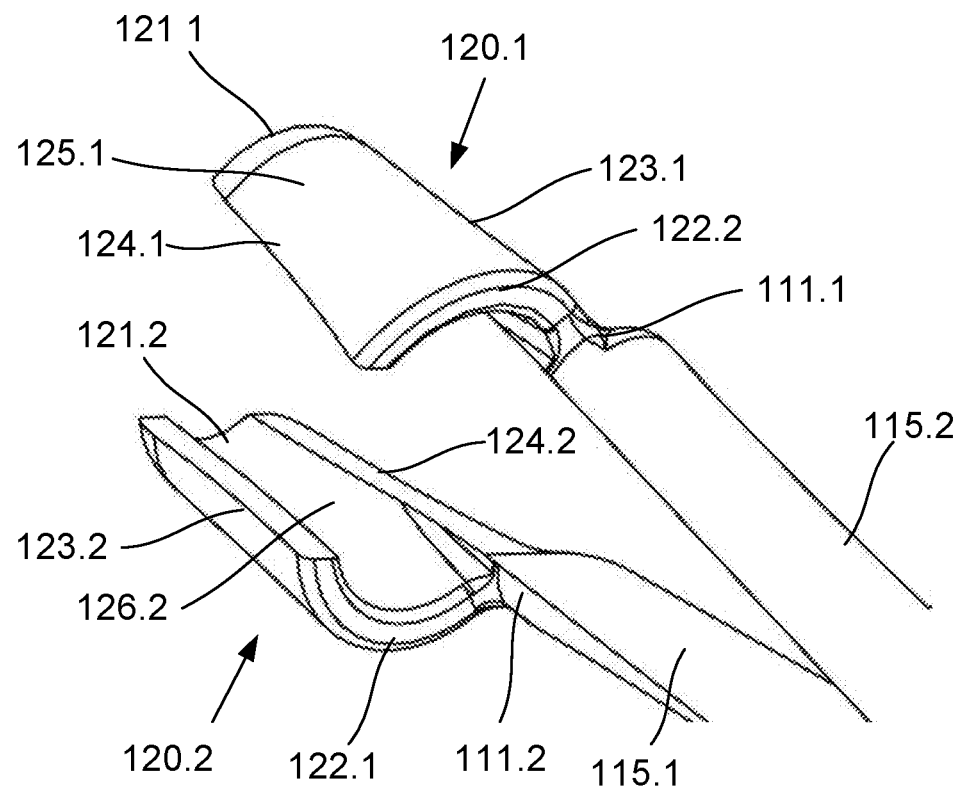
FIG. 11C is a detail view of tip members of the device of FIG. 10A.

An example process for inserting the device 800 will now be discussed with regard to FIGS. 10A to 10D. As per the process described above with regard to FIGS. 3A to 3D for a single arm version of the device 100, the process assumes the intubation device 220 has already been put into position as part of the intubation procedure, with the blade portion 222 inserted into the mouth 202 and its distal tip 223 located near the larynx 204, as shown in FIG. 10A. Then, the device 800 can be initially inserted as shown in FIG. 10B, with the arms 110.1, 110.2 in the closed position, by passing the tip members 120.1, 120.1 though the mouth 202 and moving them towards the pharynx 203. The user may move the device 800 in an arc so that the tip members 120.1, 120.2 can move through the pharynx 203 yet without interference or trauma due to contact of the other parts of the device 800 with the subject's anatomy. The tip members 120.1, 120.2 will come into proximity of the larynx 204 as shown in FIG. 10C. Once the tip members 120.1, 120.2 are in position, the arms 110.1, 110.2 can be moved to the open position by spreading the handle portions 113.1, 113.2 apart, to cause the respective engaging surfaces 125.1, 125.2 to engage with the corresponding anterior and posterior edges of the glottis and urge them apart, to thereby open the glottis from both edges, as shown in FIG. 10D.

Figure 12:
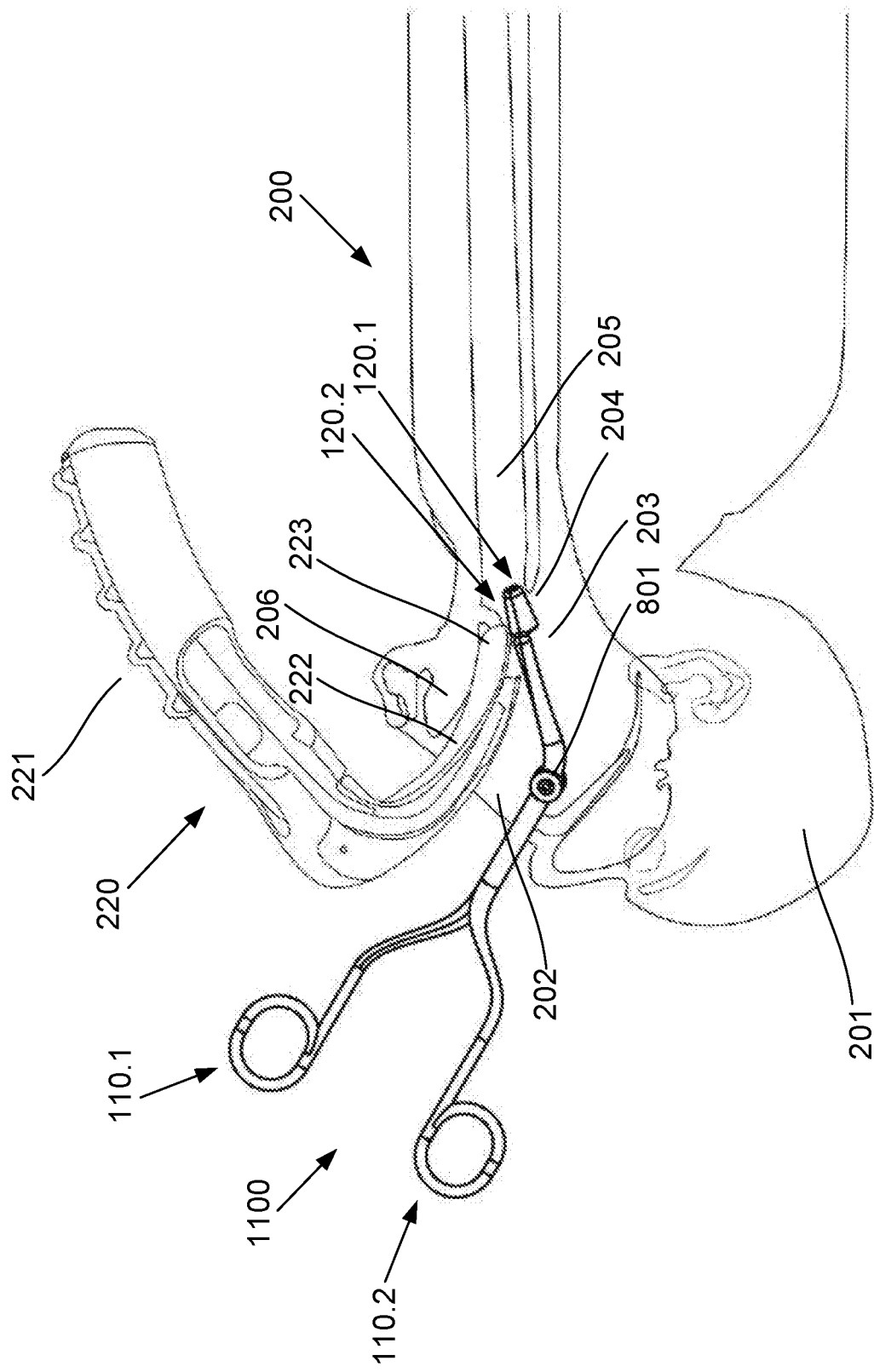
FIG. 12 is a cross section view showing the device of FIG. 10A inserted into an airway of a subject with an intubation device in an endotracheal intubation procedure.

As discussed above, the device 1100 differs from the device 800 in that the arms 110.1, 110.2 are opened by urging the handle portions 113.1, 113.2 together rather than apart. Whilst this involves reversing the tip members 120.1, 120.2 in the device 800 compared to the device 800, the device 1100 will be inserted in generally the same manner to result in an insertion position as shown in FIG. 12, where the tip members 120.1, 120.2 are still positioned proximate to the larynx and particularly in the glottis. In this case, once the tip members 120.1, 120.2 are in position, the arms 110.1, 110.2 can be moved to the open position by squeezing the handle portions 113.1, 113.2 together, to cause the respective engaging surfaces 125.1, 125.2 to engage with the corresponding anterior and posterior edges of the glottis and urge them apart, to thereby open the glottis from both edges.

As mentioned above, some embodiments of the device may be specifically adapted for guiding other devices such as an endotracheal tube rather than for manipulating anatomical structures such as the glottis. An example of a two armed device 1300 with such adaptations will now be described with regard to FIGS. 13A to 13E.

In this example, the overall geometry of the device 1300 is similar to that of the device 800, but tip members 120.1, 120.2 have a different configuration. In particular, the passageway defined by the respective tip members 120.1, 120.2 of the first arm 110.1 and the second arm 110.2 is cylindrical. Accordingly, the passageway is better suited for guiding the cylindrical endotracheal tube when the first arm 110.1 and the second arm 110.2 are in the closed position or in a slightly open position.

Figure 14:
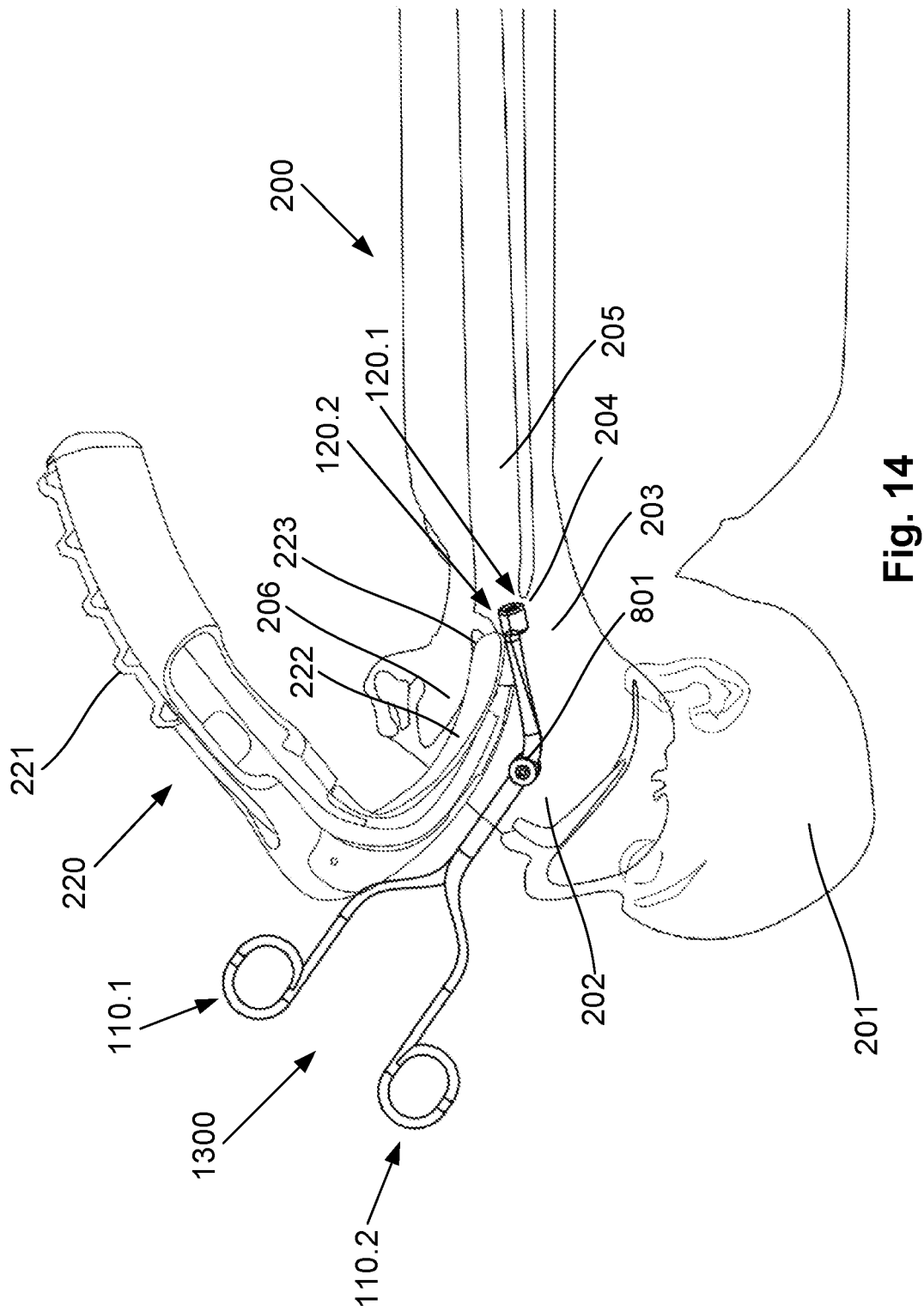
FIG. 14 is a cross section view showing the device of FIG. 13A inserted into an airway of a subject with an intubation device in an endotracheal intubation procedure.

The inserted position of the device 1300 can be seen in FIG. 14, where the tip members 120.1, 120.2 are once again positioned proximate to the larynx, but in this case the tip members 120.1, 120.2 are not used to engage the edges of the glottis but instead may be placed outside of the glottis and used to finely adjust the positioning of the endotracheal tube as it is advanced through the glottis using the intubation device 220. The tip members 120.1, 120.2 may be positioned near the distal end 223 of the blade portion 222 of the intubation device 220 so that when the endotracheal tube is advanced from the distal end 223, the endotracheal tube passes through the passageway defined by the tip members 120.1, 120.2.

The tip members 120.1, 120.2 may be moved to help to guide the advancement path of the endotracheal tube. For instance, the tip members 120.1, 120.2 may initially be positioned outside of the glottis and held in an open position for receiving the endotracheal tube as it is being advanced towards the glottis, then the tip members 120.1, 120.2 may be moved towards a closed position for gripping the endotracheal tube. The user can then move the device 1300 as required to guide the distal tip of the endotracheal tube into the glottis, and when the endotracheal tube is positioned correctly, the user may release the grip on the endotracheal tube and allow the endotracheal tube to continue to be advanced through the tip member 120.1, 120.2.

Figure 13A:
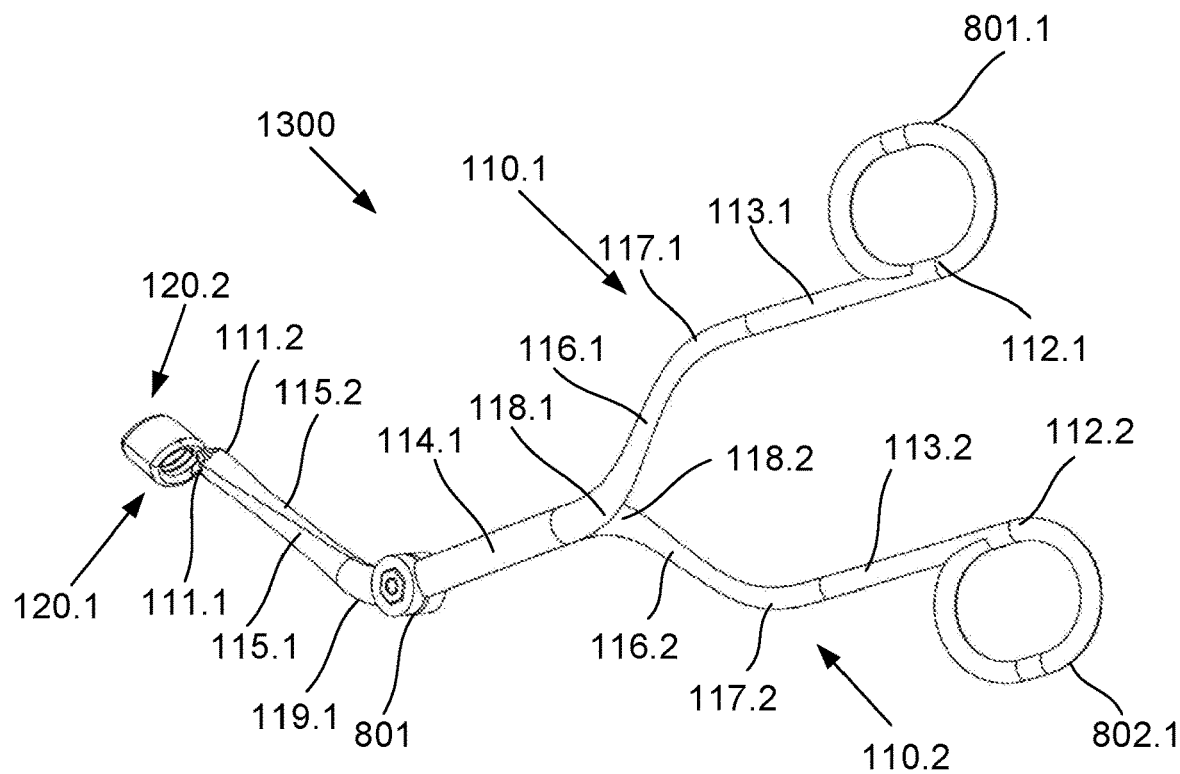
FIG. 13A is a perspective view of a sixth example of device for insertion into an airway of a subject, the device being in a closed position.
Figure 13B:
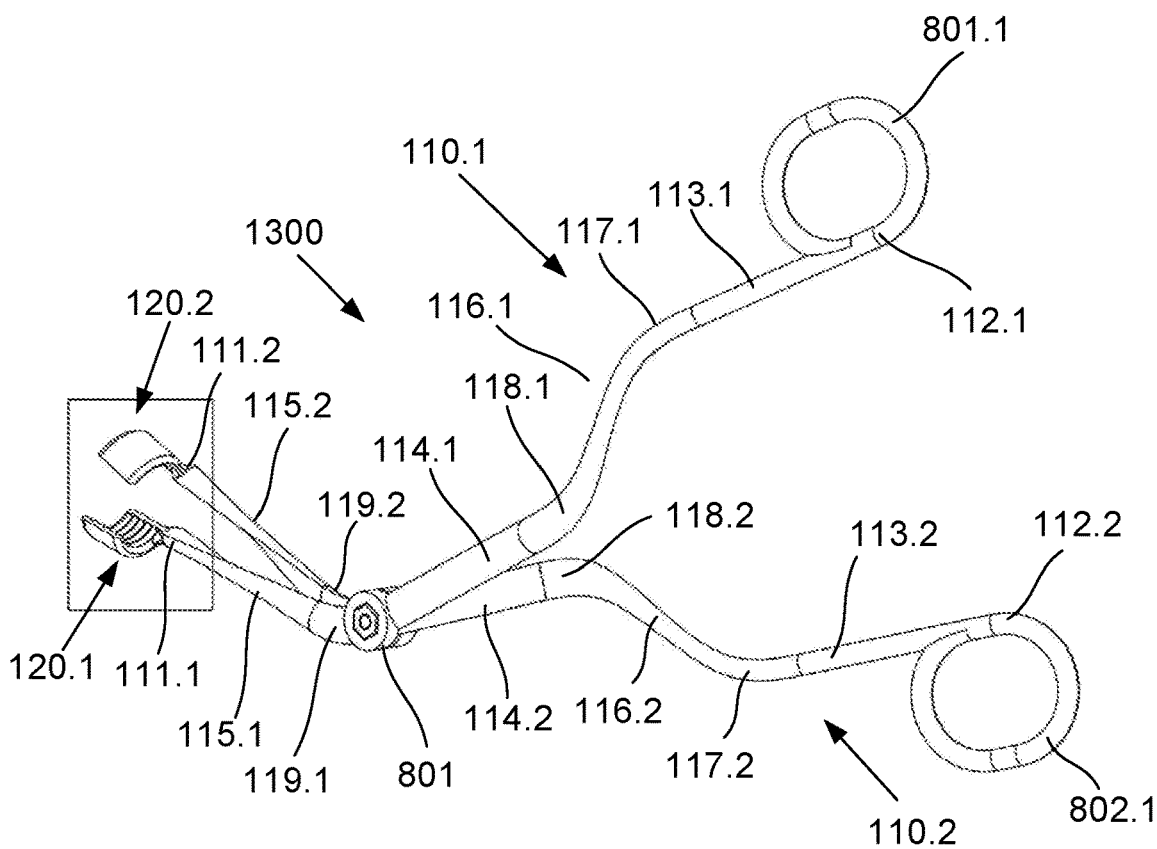
FIG. 13B is a perspective view of the device of FIG. 13A, the device being in an open position.
Figure 13C:
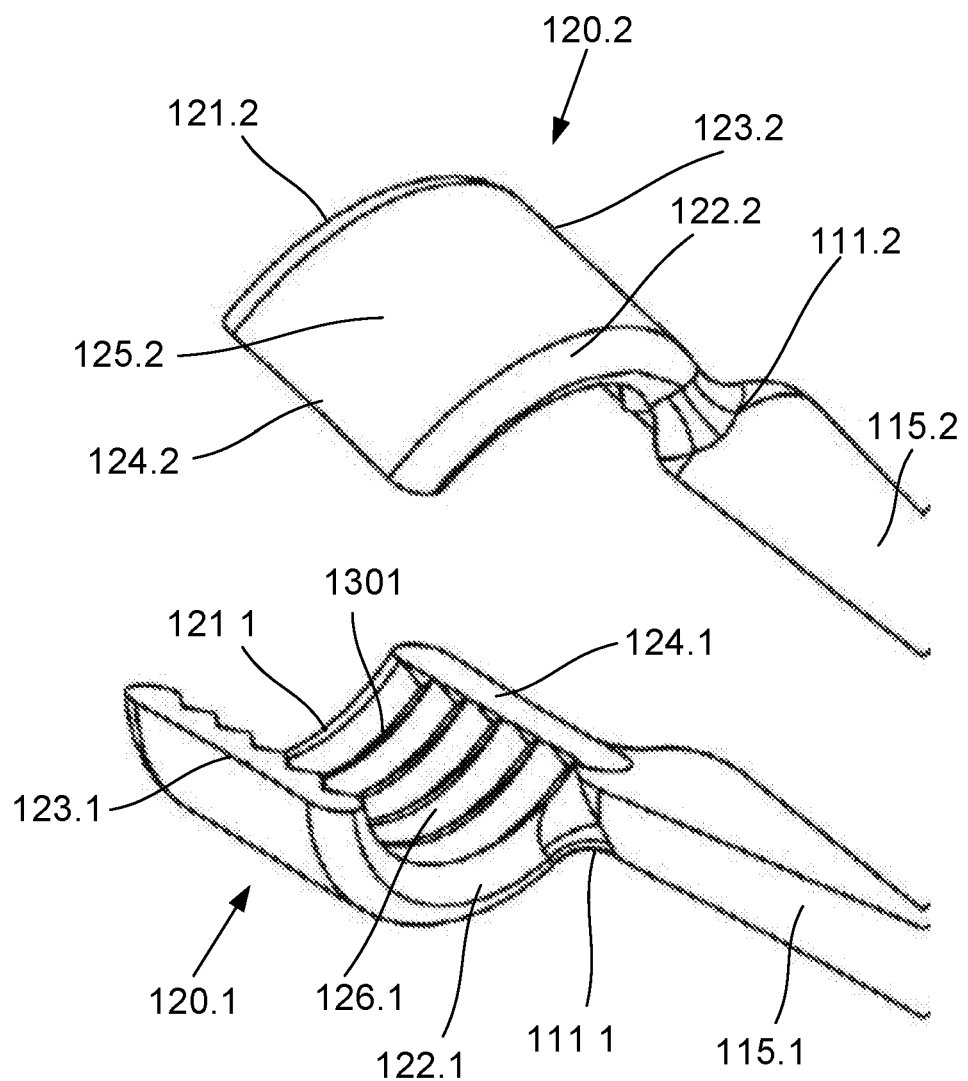
FIG. 13C is a detail view of tip members of the device of FIG. 13A.

In some examples, the respective tip members 120.1, 120.2 of the first arm 110.1 and the second arm 110.2 may include a textured surface 1301 within the cylindrical passageway, as shown in FIG. 13C. The textured surface 1301 may include ridges or other structural features which can be used to provide an improved grip on an endotracheal tube and thus allow the endotracheal tube to be more reliably manipulated or guided by the tip members 120.1, 120.2.

It will be appreciated that embodiments of the devices described above may vary in size and shape to suit subjects having different ages, sizes and anatomical configurations. For instance, different devices may be provided for use with pediatric, adult or obese subjects. In some implementations different devices may be provided to correspond to the range of different types, shapes and sizes of intubation devices blades, such that a user may select the particular device for a subject based on a selection of an intubation device blade for that subject.

In any event, the above described embodiments of the device each provide a useful capability for manipulating anatomical structures or other devices in the larynx, when performing an oral endotracheal intubation procedure using a single-handed intubation device. The devices allow the user of the intubation device to use their other hand to facilitate the intubation procedure, for example by opening the glottis or guiding the endotracheal tube. The devices have been designed to particularly allow the tip members 120.1, 120.2 to be positioned proximate to the larynx 204 whilst substantially reducing the impact on other parts of the subject's anatomical structures or the intubation device 220 in use.

Figure 15A:
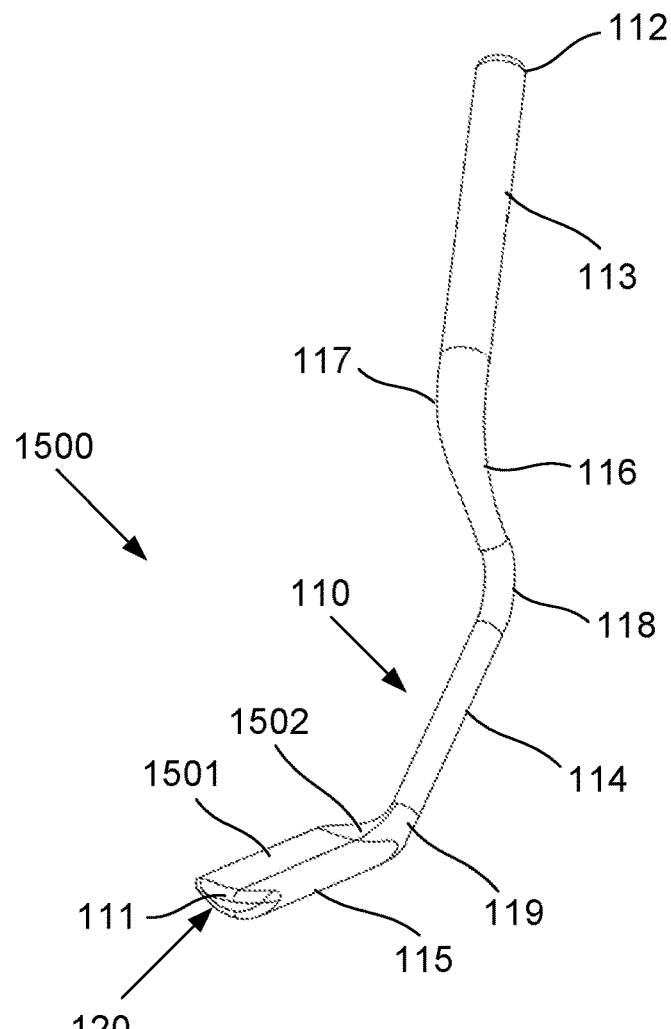
FIGS. 15A and 15B are perspective views of a seventh example of device for insertion into an airway of a subject.
Figure 15B:
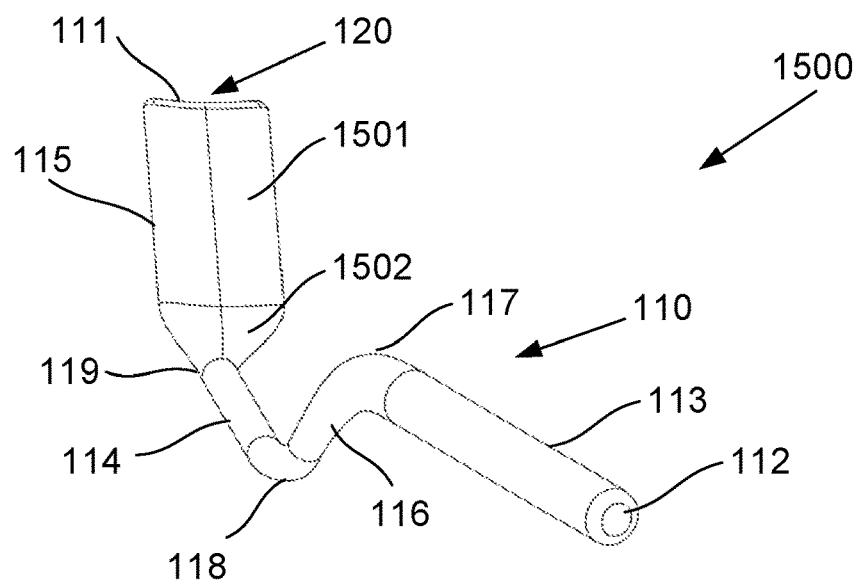

A seventh example of the device 1500 will now be described with reference to FIGS. 15A and 15B. This version of the device 1500 provides a further embodiment of a single arm device, and shares its overall geometric arrangement with the previous examples of single arm devices 100, 400, 600, therefore features corresponding to those in the previous examples have been assigned the same reference numerals.

In this case, the device 1500 does not include a protruding tip member like previous examples, rather the tip 120 coincides with the distal end 111 of the arm 110. However, in this embodiment of the device 1500, the arm 110 includes a laterally expanded section 1501 extending between the tip 120 and the offset portion 114, i.e. along the insertion portion 115. Accordingly, even though a tip member is not provided, this embodiment of the device 1500 provides an example of an alternative configuration that can nevertheless provide the user with a capability to manipulate anatomical structures inside the subject.

The laterally expanded section 1501 may include an engaging surface for engaging tissues of the subject 200, in a similar manner as described for the engaging surface in examples of the device having a tip member. In some examples, the laterally expanded section may include a convexly curved surface which provides the engaging surface.

However, the engaging surface provided by the laterally expanded section 1501 will be located partially along the arm rather than on a protruding tip member, and thus may be positioned for engaging with different anatomical structures of the subject 200. In this example, an engaging surface of the laterally expanded section 1501 may be configured for engaging with tissue in a pharynx 203 of the subject 200. For example, the laterally expanded section 1501 may be useful for pushing down a sack or pouch of the pharynx 203 in some subjects 200.

The laterally expanded section 1501 may be in the form of laterally extending wings which are substantially symmetrical about a central plane of the insertion portion 115 of the arm 110. However, in some examples, the laterally expanded section 1501 may only extend to one side of the arm 110 or may have uneven lateral wings. In this embodiment, the arm 110 also includes a tapered section 1502 between the laterally expanded section 1501 and the distal bend 119.

Figure 16A:
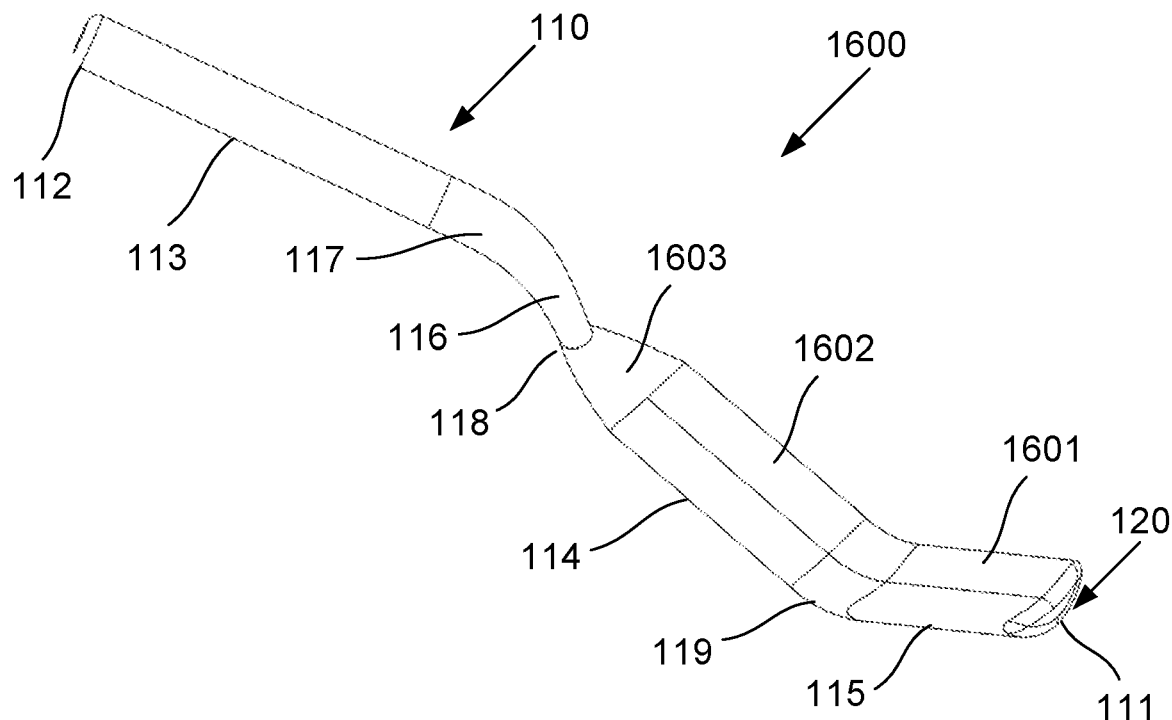
FIGS. 16A and 16B are perspective views of an eighth example of device for insertion into an airway of a subject.
Figure 16B:
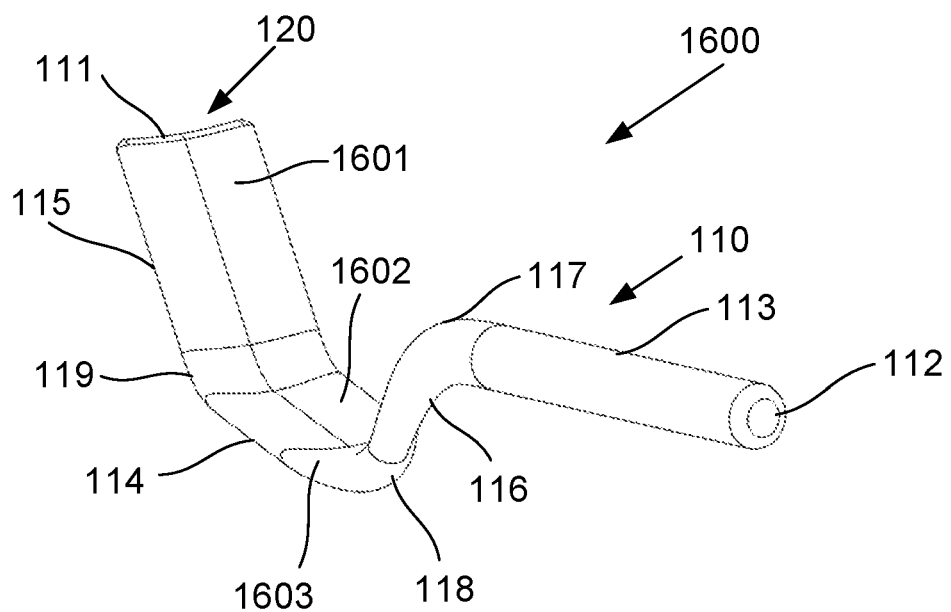

Other examples may include an extended laterally expanded section. To illustrate this, an eighth example of the device 1600 will now be described with reference to FIGS. 16A and 16B. This version of the device 1600 shares its overall geometric arrangement with the previous example of the device 1500 and the other single arm versions of the device as mentioned above, and therefore features corresponding to those in the previous examples have been assigned the same reference numerals.

In this example of the device 1600, the laterally expanded section extends at least partially along the offset portion 114. Thus, the arm 110 includes a first laterally expanded section 1601 extending between the tip 111 and the offset portion 114, i.e. along the insertion portion 115, and a second laterally expanded section 1602 extending at least partially along the offset portion 114. The arm 110 also includes a tapered section 1603 between the second laterally expanded section 1602 and the intermediate bend 118.

In any event, this example of the device 1600 can have similar functionality as the previous example of the device 1500, whereby the laterally expanded section may be used to engage with tissue in the pharynx 203. In this case, the second laterally expanded section 1602 provides an extended engaging surface for also providing a capability for engaging tissues in the back of the subject's mouth 102.

Figure 17A:
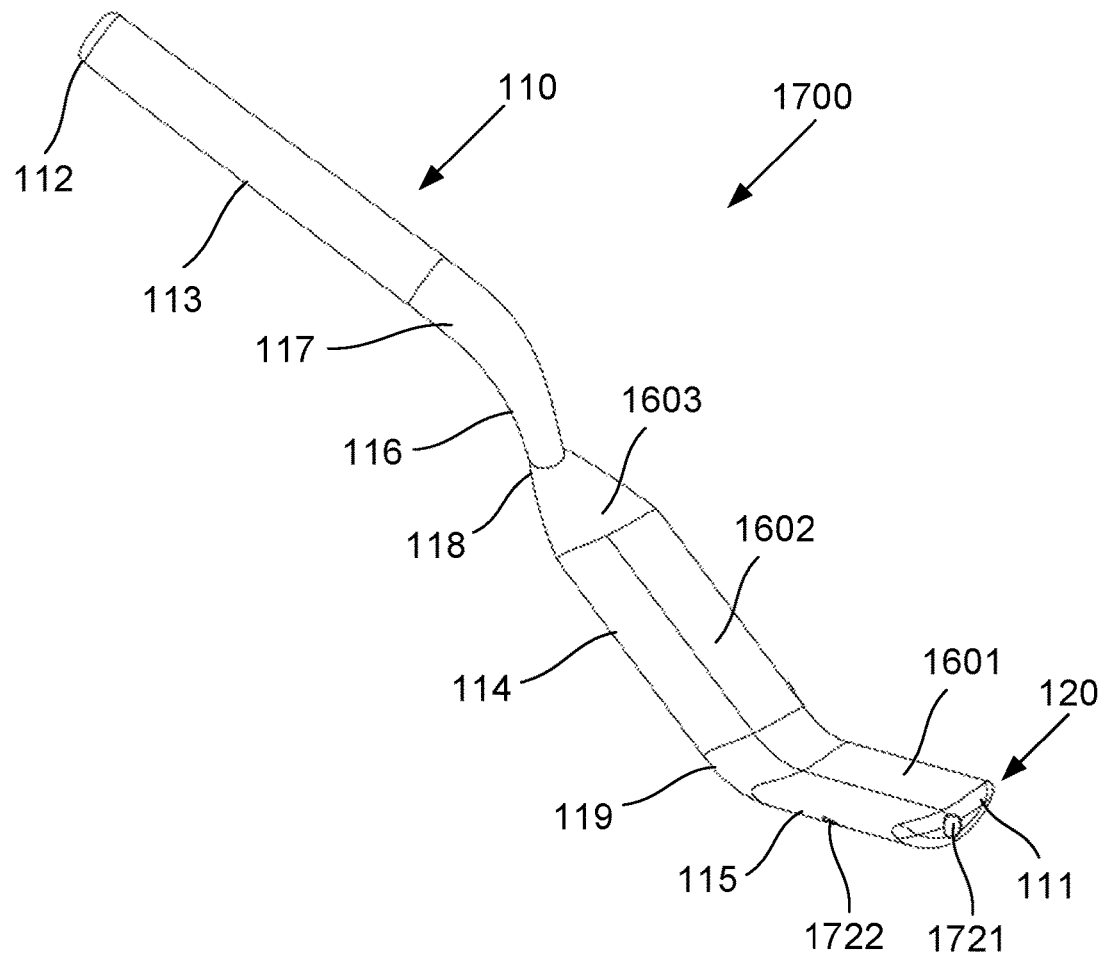
FIGS. 17A and 17B are perspective views of a ninth example of device for insertion into an airway of a subject.

A ninth example of the device 1700 will now be described with reference to FIGS. 17A and 17B. In this case, the arm includes one or more suction ports 1721, 1722 located proximate to the distal end 111. The suction ports 1721, 1722 are in fluid communication with a suction conduit (not shown) extending at least partially along the arm 110. In this case, the suction conduit extends inside the arm 110 as a hollow passageway extending through the arm 110. Otherwise, the external configuration of this version of the device 1700 is substantially the same as the previous example of the device 1600 and therefore features corresponding to those in the previous example have been assigned the same reference numerals.

Figure 17B:
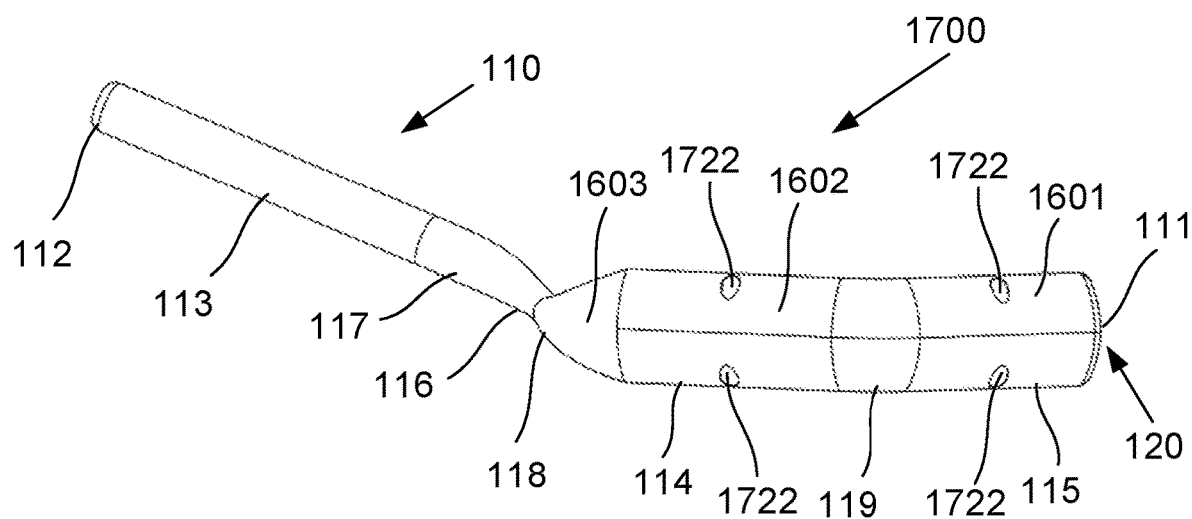

As best seen in FIG. 17B, the arm includes an tip suction port 1721 positioned at the tip 120, and two pairs of additional suction ports 1722 positioned in the first and second laterally expanded sections 1601, 1602. A proximal end of the suction conduit may be coupled to a suction source, typically via the proximal end 112 of the arm 110, to thereby allow suction through the suction ports 1721, 1722, which will be positioned near parts of the subject's anatomy in use.

Figure 18:
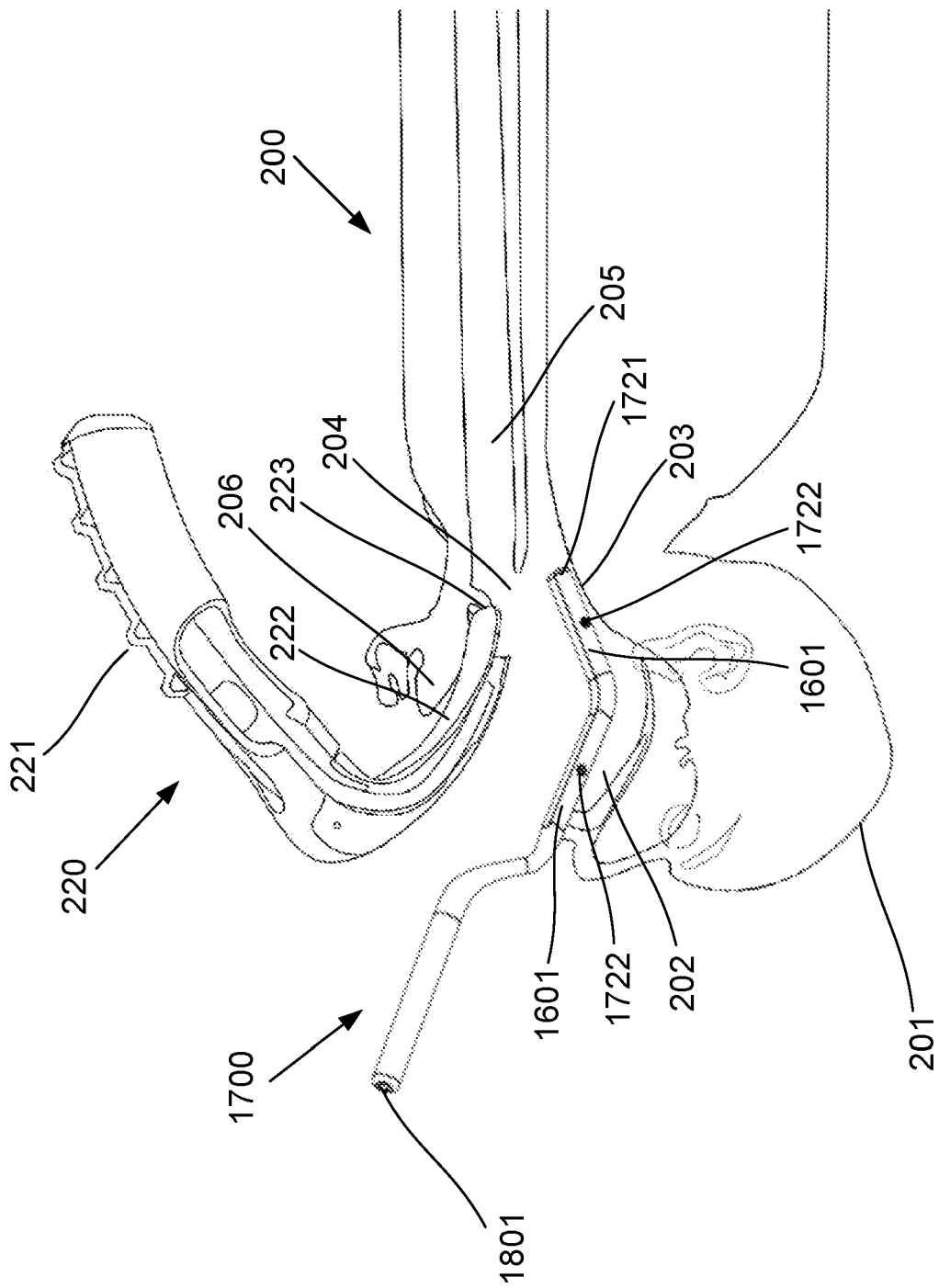
FIG. 18 is a cross section view showing the device of FIGS. 17A and 17B inserted into an airway of a subject with an intubation device in an endotracheal intubation procedure.

This capability to provide suction in use is further illustrated in FIG. 18, which shows an example of the device 1700 inserted into the airway of the subject 200 with an intubation device 220. A suction connection 1801 can be seen at the proximal end 112 of the arm 110, which would be coupled to a suction source (not shown) in use to provide suction via the suction ports 1721, 1722.

As shown in FIG. 18, the first laterally expanded section 1601 of the device 1700 may be urged into engagement with tissues in the pharynx, separated dorsally from the blade portion 222 of the intubation device 220. This can effectively open up the subject's airway, including allowing an improved view of the larynx 204 and even the oesophagus. Thus, this device 1700 can be used to push dorsally on the pharynx 203, pushing in the opposite direction compared to the blade portion 222 of the intubation device 220 (which is typically lifted forwards relatively to the subject in use).

It will be appreciated that the tip suction port 1721 can provide suction near the larynx 204, whilst the additional suction ports 1722 provided in the laterally expanded sections 1601, 1602 can provide suction in the pharynx 203 and mouth 202 of the subject, preferably in the vicinity of salivary glands in these regions. However, different configurations of suction ports may be provided to allow suction relative to different parts of the subject's anatomy, depending on requirements.

Figure 19A:
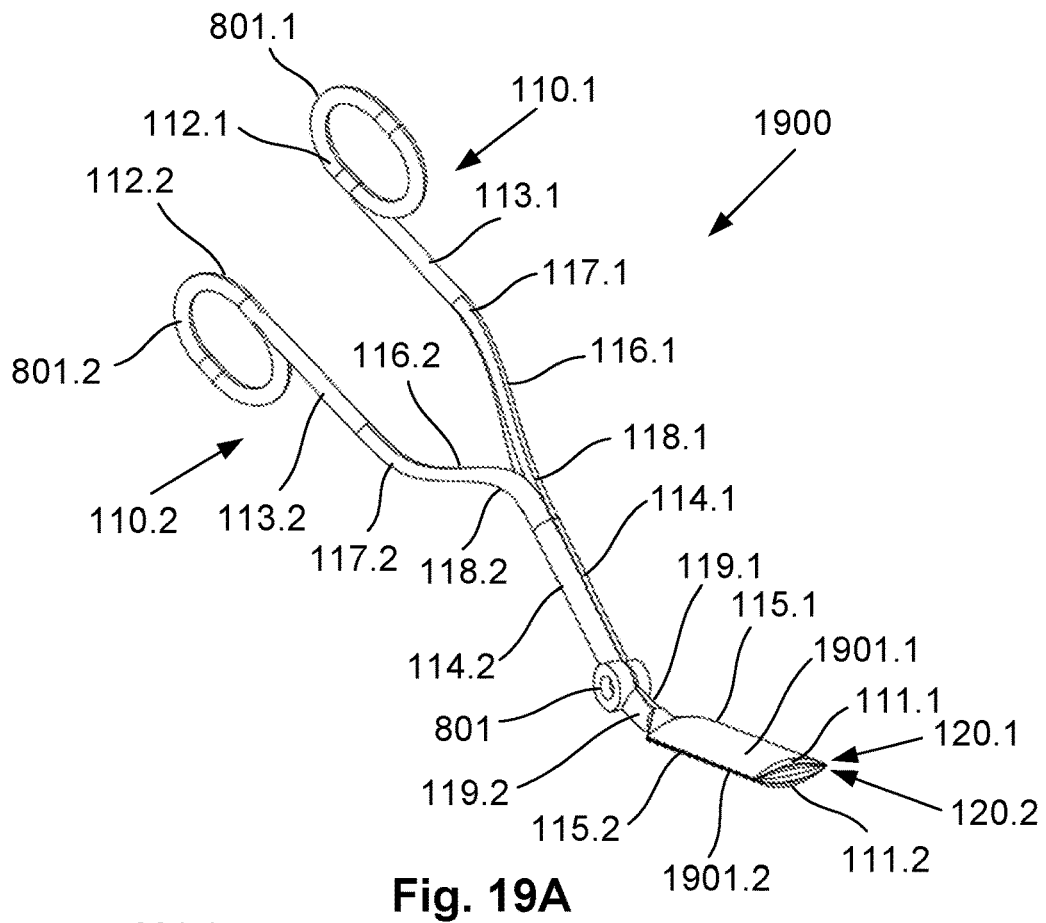
FIGS. 19A and 19B are perspective views of a tenth example of device for insertion into an airway of a subject; and, FIGS. 20A and 20B are perspective views of an eleventh example of device for insertion into an airway of a subject.
Figure 19B:
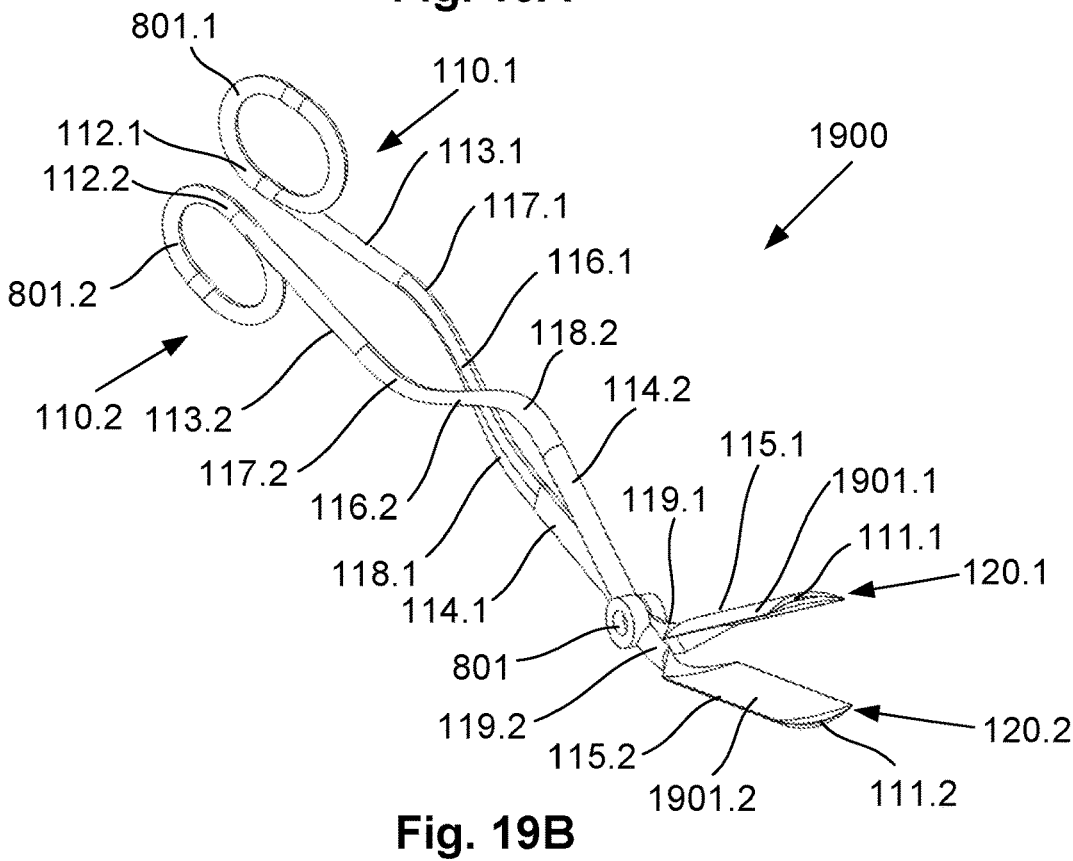

Two armed versions of the device may also be adapted to have laterally expanded sections in a similar manner as per the above examples. To illustrate this, a tenth example of the device 1900 will now be described with reference to FIGS. 19A and 19B. This version of the device 1900 has an overall geometry similar to that of the previously described device 1100 (being another example of a two armed device in which the first arm 110.1 and the second arm 110.2 are moved into the open position by urging the handle portions 113.1, 113.2 together), and therefore features corresponding to those in the previous example have been assigned the same reference numerals.

In this case, the arms 110.1 and 110.2 of the device 1900 do not have protruding tip members but have tips 120.1, 120.2 coinciding with respective distal ends 111.1, 111.2 of the arms 110.1, 110.2. However, in this embodiment, the insertion portions 115.1 and 115.2 of each arm 110.1, 110.2 each have laterally expanded sections 1901.1 and 1901.2, in a similar manner as the previous single armed example device 1500. As in that previous example, the laterally expanded sections 1901.1, 1901.2 may have engaging surfaces for engaging tissues in the pharynx 203, and in this case also the tongue 206, which can be of assistance, for example, during an endotracheal intubation procedure.

In use, the device 1900 may be inserted with the tips 111.1 and 111.2 positioned proximate to the larynx, and then the arms 110.1 and 110.2 may be moved towards the open position such the laterally expanded section 1901.1 of the first arm 110.1 will engage with the tongue 206 and urge it anteriorly (i.e. lift it forward), whilst the laterally expanded section 1901.2 of the second arm 110.2 will engage with the pharynx and urge it posteriorly (i.e. push it down). It will be appreciated that this can help to open up the airway of the subject to allow improved visualisation and access for the endotracheal intubation procedure.

Figure 20A:
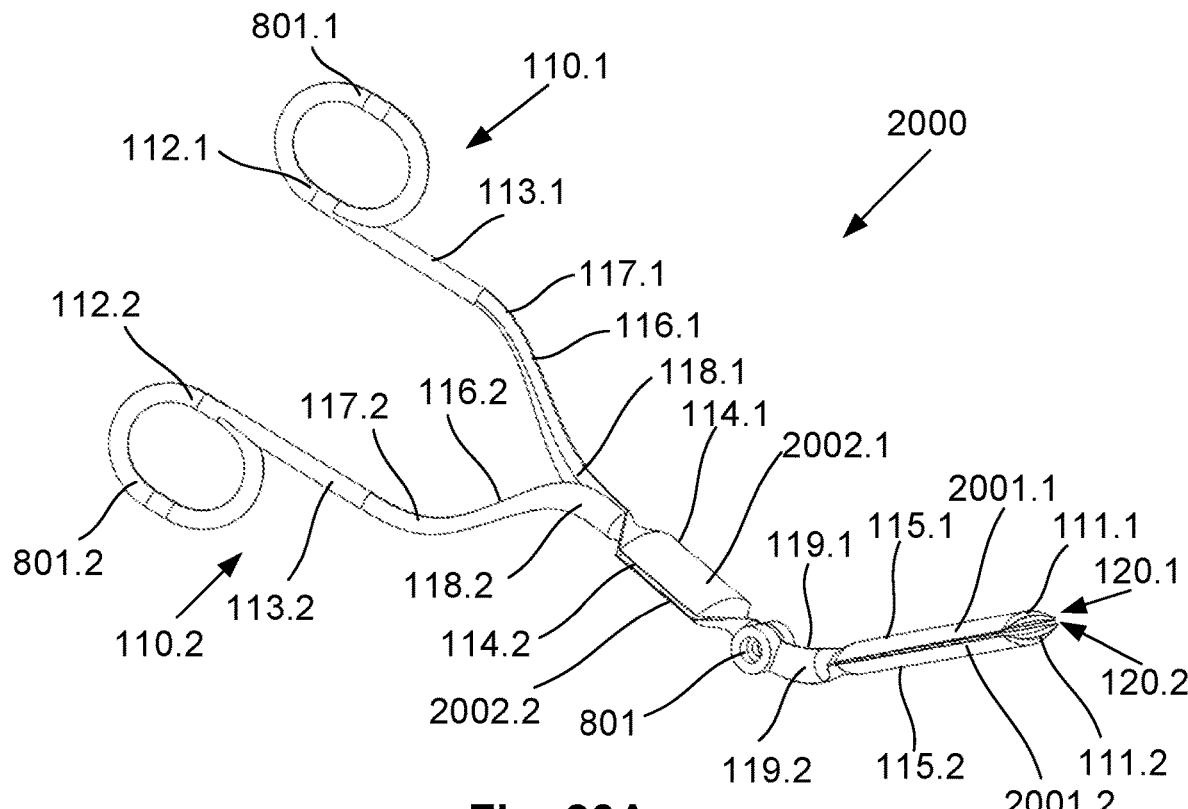
Figure 20B:
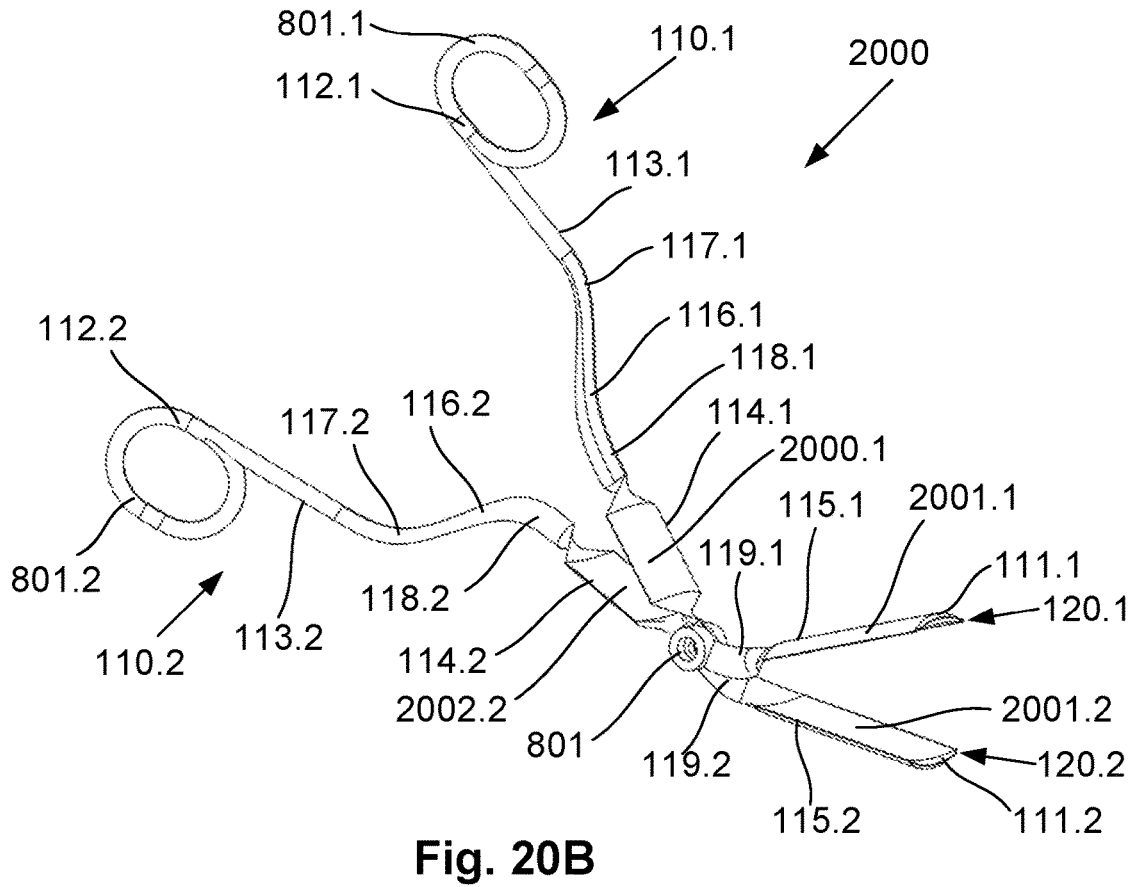

An eleventh example of the device 2000 will now be described with reference to FIGS. 20A and 20B. This version of the device 2000 has an overall geometry similar to that of the previous example devices 800 and 1300 (being another example of a two armed device in which the first arm 110.1 and the second arm 110.2 are moved into the open position by urging the handle portions 113.1, 113.2 apart), and therefore features corresponding to those in the previous example have been assigned the same reference numerals.

As per the last example device 1900, the arms 110.1 and 110.2 of the device do not have protruding tip members but have tips 120.1, 120.2 coinciding with respective distal ends 111.1, 111.2 of the arms 110.1, 110.2. In this embodiment, the insertion portions 115.1 and 115.2 of each arm each have laterally expanded sections 2001.1 and 2001.2, as per the previous example of the device 1900. Furthermore, the offset portions 114.1, 114.2 each have additional laterally expanded sections 2002.1 and 2002.2, which can provide additional capability for engaging tissues in the subject's pharynx 203, tongue 206 and other parts of the mouth 202.

It is noted that the first and second laterally expanded sections 2001.1 and 2001.2 of each arm 110.1, 110.2 are provided separately on either side of the pivot 801, in contrast to the previous single armed version 1600 where the second laterally expanded section 1602 is formed as a continuous extension of the first laterally expanded section 1601.

In some other embodiments of the device, the arm 110 (or arms 110.1, 110.2) may include a moveable arm portion (not shown) at the distal end 111. The moveable arm portion may be configured to vary the effective shape and/or the curvature of the arm as required to suit different subject anatomies or to allow fine tuning of the position and direction of the tip 120 of the device during an intubation procedure. This can be used to engage anatomy of the subject and adjust the advancement path of the endotracheal tube during an endotracheal intubation procedure. The moveable blade portion can also be used to enhance the ability of the user to manipulate the tongue or other anatomical features of the subject during a procedure, without needing to mover the entire device using the handle.

The moveable blade portion may be implemented by providing one or more articulated arm segments. The arm segment (or segments) may be connected to the arm and adjacent arm segments by pivot joints. The device may also include a movement interface (not shown) proximate to the handle 113 (or one of the handles 113.1, 113.2) for allowing a user to cause the moveable arm portion to move using the movement interface.

In one example the movement interface is a lever coupled to the handle 113. For example, the arm segments may be coupled to the lever using a cable or the like, so that activation of the lever will effectively shorten the cable and cause the arm segments to articulate relative to the subject. In any event, it will be appreciated that a range of different configurations of one or more moveable arm segments can be used whilst conforming to the overall geometry and functionality of the device as described above.

It will also be appreciated that manipulator devices similar to those described above may enable advantageous new methods for use in endotracheal intubation procedures, involving the simultaneous use of an intubation device and a manipulator device.

In one example, a method for use in an endotracheal intubation procedure for delivering an endotracheal tube into a trachea of a subject may be performed using an intubation device and a manipulator device, in which the intubation device includes a laryngoscope blade, a handle attached to the blade, and a channel extending at least along the blade and having an outlet proximate to a blade tip that allows a distal end of the endotracheal tube to be advanced from the outlet, and in which the manipulator device includes an arm with a handle portion at a proximal end and a tip member protruding from a distal end of the arm.

In this example, the method may involve an initial step of a user holding the intubation device by the handle in a first hand and moving the handle to insert the blade of the intubation device into a mouth of the subject so that the blade tip is positioned proximate to a larynx of the subject. The method will also include the user holding the manipulator device by the handle portion in a second hand and moving the handle portion to insert the distal end of the arm of the manipulator device into the mouth of the subject adjacent to the blade of the intubation device, and move the tip member through the mouth and pharynx of the subject to thereby position the tip member proximate to the larynx of the subject. Finally, the method will include advancing the endotracheal tube from the outlet of the intubation device while using the tip member to manipulate an anatomical structure in at least one or the larynx, pharynx and the mouth of the subject and/or guide movement of the endotracheal tube.

It will be appreciated that such a method may utilise any of the above described embodiments of the manipulator devices, although other suitable forms of manipulator devices may also be used.

Similarly, it will be appreciated that such a method may utilise any suitable form of intubation device. In some examples, the intubation device may be a conventional laryngoscope, or any one of a wide range of currently available intubation devices which operate by advancing the endotracheal tube through a channel extending along its blade.

However, it will be particularly advantageous to implement the above discussed method using a single handed intubation device, such as that described in WO/2016/090435A1. In broad terms, such a single handed intubation device may include a tube movement mechanism that moves the endotracheal tube through the channel to thereby advance the endotracheal tube. In particular, the tube movement mechanism may include a digit interface that allows the user to operate the tube movement mechanism using a digit of the same hand that is holding the intubation device. Accordingly, implementations of the method using a single handed intubation device may include the user holding the intubation device by the handle and using the digit interface to advance the endotracheal tube into the trachea of the patient using the first hand, while holding the manipulator device by the handle portion using the second hand.

In one specific implementation, the method may include using the tip member to urge a posterior edge of the glottis posteriorly relative to the subject to thereby open the glottis. It will be appreciated that this may utilise the embodiment of the device 100 described above with reference to FIGS. 1A to 1E, where examples of the positioning of the intubation device and manipulator device during the method are shown in FIGS. 3A to 3D.

In another specific implementation, the method may involve the use of a manipulator device having two arms, such as per the embodiment of the device 800 described above with reference to FIGS. 8A to 8F. In the context of the above discussed method, the arm defines a first arm of the manipulator device and the manipulator device further includes a second arm pivotally attached to the first arm at a pivot point located between the tip and the handle portion. The second arm includes a second handle portion at a proximal end of the second arm and a second tip member protruding from a distal end of the second arm. As discussed above, the first arm and the second arm may be moveable about the pivot point between a closed position and an open position. Accordingly, the method may include using the first and second tip members to engage anterior and posterior edges of the glottis and open the glottis by urging the anterior edge anteriorly and posterior edge posteriorly when the first arm and the second arm are moved from the closed position to the open position. Examples of the positioning of the intubation device and manipulator device during this version of the method are shown in FIGS. 10A to 10D.

In yet other implementations, the method may include guiding movement of a tip of the endotracheal tube into the larynx, such as by using the two armed manipulator device 1300 described above with regard to FIGS. 13A to 13E.

In any event, it will be appreciated that the methods discussed above involving the use of a manipulator device with an intubation device can facilitate easier delivery of an endotracheal tube by manipulating anatomical structures proximate to the larynx and/or guiding the endotracheal tube through the larynx.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers. As used herein and unless otherwise stated, the term "approximately" means±20%.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

It will of course be realised that whilst the above has been given by way of an illustrative example of this invention, all such and other modifications and variations hereto, as would be apparent to persons skilled in the art, are deemed to fall within the broad scope and ambit of this invention as is herein set forth.

The claims defining the invention are as follows:

1. A device for insertion into an airway of a subject, the device including:
    a) an arm defining a distal end and a proximal end, the arm including:
        i) an elongate handle portion at the proximal end, the handle portion extending substantially towards the distal end; and
        ii) an offset portion located between the distal end and the handle portion, the offset portion being offset dorsally relative to the handle portion and the distal end;
        iii) an angled portion between the handle portion and the offset portion, the angled portion being oriented at an angle relative to the handle portion;
        iv) a proximal bend between the handle portion and the angled portion;
        v) an intermediate bend between the angled portion and the offset portion; and
        vi) a distal bend between the offset portion and the insertion portion; and
    b) a tip at the distal end of the arm, wherein the arm is configured to allow a user to hold the handle portion outside of a mouth of the subject and move the handle portion to move the tip through the mouth and pharynx of the subject to thereby position the tip proximate to a larynx of the subject.

2. A device according to claim 1, wherein the arm includes an elongate insertion portion at the distal end, wherein the insertion portion is oriented at an obtuse angle relative to the handle portion.

3. A device according to claim 1, wherein the offset portion includes an elongate section and wherein the handle portion and the elongate section of the offset portion extend along respective frontal planes that are approximately parallel to and offset from one another.

4. A device according to claim 1, wherein the tip includes a tip member protruding from the distal end of the arm.

5. A device according to claim 4, wherein the tip member protrudes distally and laterally from the distal end.

6. A device according to claim 4, wherein the tip member is configured for manipulating an anatomical structure in the larynx, and wherein the tip member includes an engaging surface.

7. A device according to claim 6, wherein
    a) the engaging surface is convexly curved; and
    b) the tip member includes an opposing surface that opposes the engaging surface and that is concavely curved.

8. A device according to claim 6, wherein at least one of:
    a) the engaging surface is for engaging with a glottis of the subject; and
    b) the engaging surface is for urging a posterior edge of the glottis posteriorly relative to the subject to thereby open the glottis.

9. A device according to claim 6, wherein the engaging surface is for engaging with an epiglottic vallecula of the subject, and wherein at least one of:
    a) the engaging surface is for urging the epiglottic vallecula posteriorly relative to the subject;
    b) the engaging surface faces dorsally;
    c) the engaging surface is for urging the epiglottic vallecula anteriorly relative to the subject to thereby open the larynx; and
    d) the engaging surface faces ventrally.

10. A device according to claim 4, wherein the tip member is configured for guiding movement of another device inserted into the larynx.

11. A device according to claim 10, wherein the tip is configured for guiding movement of at least one of:
    a) an endotracheal tube being inserted into the larynx;
    b) an endotracheal tube being inserted by another device into the larynx; and
    c) a tip of an endotracheal tube being inserted by another device into the larynx.

12. A device according to claim 4, wherein at least one of:
    a) the tip member is one of paddle shaped and spoon shaped;
    b) the tip member includes a notch in a distal edge of the tip member; and
    c) the tip member is laterally tapered.

13. A device according to claim 1, wherein the arm includes a laterally expanded section extending between the tip and the offset portion, and wherein at least one of:
    a) the laterally expanded section extends at least partially along the offset portion;
    b) the laterally expanded section includes a convexly curved surface; and
    c) at least one surface of the laterally expanded section is for engaging with tissue in a pharynx of the subject.

14. A device according to claim 1, wherein the arm includes a moveable arm portion at the distal end, and wherein the device includes a movement interface proximate to the handle for allowing a user to cause the moveable arm portion to move using the movement interface.

15. A device for insertion into an airway of a subject, the device including:

a) a first arm defining a distal end and a proximal end, the first arm including:
   i) an elongate handle portion at the proximal end, the handle portion extending substantially towards the distal end; and
   ii) an offset portion located between the distal end and the handle portion, the offset portion being offset dorsally relative to the handle portion and the distal end; and
   iii) a first tip at the distal end of the first arm, wherein the arm is configured to allow a user to hold the handle portion outside of a mouth of the subject and move the handle portion to move the tip through the mouth and pharynx of the subject to thereby position the tip proximate to a larynx of the subject;
b) a second arm pivotally attached to the first arm at a pivot point located between the first tip and the handle portion, and wherein the second arm defines a distal end and a proximal end, the second arm including:
   i) an elongate second handle portion at the proximal end;
   ii) an second offset portion located between the distal end and the second handle portion, the second offset portion being offset ventrally relative to the second handle portion; and
   iii) a second tip at the distal end.

16. A device according to claim 15, wherein at least one of:
   a) the respective handle portions of the first arm and the second arm each include a loop for receiving a digit of a hand of a user; and
   b) the pivot point is located between the respective tips and offset portions of the first arm and the second arm.

17. A device according to claim 15, wherein the first arm and the second arm are moveable about the pivot point between a closed position and an open position.

18. A device according to claim 17, wherein the first arm and the second arm are configured to move from the closed position to the open position when the respective first and second handle portions are one of:
   a) urged together; and
   b) urged apart.

19. A device according to claim 17, wherein at least one of:
   a) when the first arm and the second arm are in the closed position, the respective tips and offset portions of the first arm and the second arm are substantially collocated; and
   b) wherein when the first arm and the second arm are in the closed position, the second handle portion extends substantially parallel to the first handle portion.

20. A device according to claim 17, wherein the tip of each arm includes a respective tip member protruding from the distal end of the arm, and wherein the respective tip members of the first arm and the second arm have opposing shapes.

21. A device according to claim 20, wherein the respective tip members are configured for engaging anterior and posterior edges of the glottis and opening the glottis by urging the anterior edge anteriorly and posterior edge posteriorly when the first arm and the second arm are moved from the closed position to the open position.

22. A device according to claim 20, wherein when the first arm and the second arm are in the closed position, a passageway is defined between the respective tip members of the first arm and the second arm, and wherein one of:
   a) the passageway defined by the respective tip members of the first arm and the second arm is distally tapered;
   b) the passageway defined by the respective tip members of the first arm and the second arm is cylindrical; and
   c) the respective tip members of the first arm and the second arm include a textured surface within the cylindrical passageway.

23. A device according to claim 15, wherein each of the first arm and the second arm includes, respectively:
   a) an angled portion between the handle portion and the offset portion, the angled portion being oriented at an angle relative to the handle portion;
   b) a proximal bend between the handle portion and the angled portion;
   c) an intermediate bend between the angled portion and the offset portion; and
   d) a distal bend between the offset portion and the insertion portion.

24. A device for insertion into an airway of a subject, the device including:
   a) an arm defining a distal end and a proximal end, the arm including:
      i) an elongate handle portion at the proximal end, the handle portion extending substantially towards the distal end; and
      ii) an offset portion located between the distal end and the handle portion, the offset portion being offset dorsally relative to the handle portion and the distal end, wherein the distal end and the offset portion extend along a sagittal plane and the handle portion extends laterally outwardly from the sagittal plane at an angle that is at least one of:
         (1) between 0° and 90°;
         (2) between 15° and 45°;
         (3) between 25° and 30°; and
         (4) about 27°; and
   b) a tip at the distal end of the arm, wherein the arm is configured to allow a user to hold the handle portion outside of a mouth of the subject and move the handle portion to move the tip through the mouth and pharynx of the subject to thereby position the tip proximate to a larynx of the subject.

* * * * *